(12) United States Patent
Goldstein et al.

(10) Patent No.: US 10,429,377 B1
(45) Date of Patent: Oct. 1, 2019

(54) COAGULATION TEST DEVICE, SYSTEM, AND METHOD OF USE

(71) Applicant: Coagulation Sciences LLC, Riverdale, NY (US)

(72) Inventors: Sheldon Goldstein, Riverdale, NY (US); Michael Kagan, Riverdale, NY (US); Nicholas Lauder, Riverdale, NY (US); Maury D. Cosman, Riverdale, NY (US)

(73) Assignee: COAGULATION SCIENCES LLC, Riverdale, NY (US)

( * ) Notice: Subject to any disclaimer, the term of this patent is extended or adjusted under 35 U.S.C. 154(b) by 0 days.

(21) Appl. No.: 16/355,081

(22) Filed: Mar. 15, 2019

(51) Int. Cl.
*G01N 33/49* (2006.01)
*G01N 33/50* (2006.01)
*G01R 33/07* (2006.01)
*G01N 33/52* (2006.01)
*B01L 3/00* (2006.01)

(52) U.S. Cl.
CPC ......... *G01N 33/4905* (2013.01); *G01N 33/50* (2013.01); *G01R 33/072* (2013.01); *B01L 3/5027* (2013.01); *B01L 2200/10* (2013.01); *B01L 2300/0816* (2013.01); *B01L 2300/0819* (2013.01); *G01N 33/521* (2013.01)

(58) Field of Classification Search
None
See application file for complete search history.

(56) References Cited

U.S. PATENT DOCUMENTS

| | | | |
|---|---|---|---|
| 2,616,796 | A | 11/1952 | Schilling et al. |
| 2,738,606 | A | 3/1956 | Klein |
| 3,302,452 | A | 2/1967 | Leslie |
| 3,695,482 | A | 10/1972 | Smith |
| 3,836,333 | A | 9/1974 | Mintz |
| 3,918,908 | A | 11/1975 | Moyer et al. |
| 4,000,972 | A | 1/1977 | Braun et al. |
| 4,074,971 | A | 2/1978 | Braun et al. |
| 4,105,411 | A | 8/1978 | Biver |
| 4,125,327 | A | 11/1978 | Margolis |
| 4,135,819 | A | 1/1979 | Schmid-Schonbein |
| 4,443,408 | A | 4/1984 | Mintz |
| 4,497,774 | A | 2/1985 | Scordato |

(Continued)

FOREIGN PATENT DOCUMENTS

| | | |
|---|---|---|
| CN | 101970684 A | 2/2011 |
| DE | 3540661 A1 | 5/1987 |

(Continued)

OTHER PUBLICATIONS

Austen et al., "Laboratory Diagnosis of Blood Coagulation Disorders," Human Blood Coagulation, Haemostasis and Thrombosis, Third Edition, 1984, Chapter 9, pp. 170-179.

(Continued)

*Primary Examiner* — Jennifer Wecker
(74) *Attorney, Agent, or Firm* — Michael Best & Friedrich LLP

(57) ABSTRACT

A coagulation test device for measuring clotting time and clot characteristics of a whole blood sample under different hemostatic conditions. Results of the test are used as an aid in management of patients with coagulopathy of unknown etiology in order to help the physician determine appropriate clinical action to arrest bleeding in a patient.

24 Claims, 15 Drawing Sheets

(56) References Cited

U.S. PATENT DOCUMENTS

| | | | |
|---|---|---|---|
| 4,534,939 A | 8/1985 | Smith et al. | |
| 4,640,896 A | 2/1987 | Farrell et al. | |
| 4,659,550 A | 4/1987 | Schildknecht | |
| 4,663,127 A | 5/1987 | Jackson et al. | |
| 4,671,939 A | 6/1987 | Mintz | |
| 4,752,449 A | 6/1988 | Jackson et al. | |
| 4,756,884 A | 7/1988 | Hillman et al. | |
| 4,782,026 A | 11/1988 | Baugh et al. | |
| 4,865,984 A | 9/1989 | Nemerson et al. | |
| 4,871,677 A | 10/1989 | Baugh et al. | |
| 4,946,775 A | 8/1990 | Yin | |
| 5,039,615 A | 8/1991 | Takahata | |
| 5,302,348 A | 4/1994 | Cusack et al. | |
| 5,366,869 A | 11/1994 | Goldstein | |
| 5,637,087 A | 6/1997 | O'Neil et al. | |
| 5,768,407 A | 6/1998 | Shen et al. | |
| 5,951,951 A | 9/1999 | Lane et al. | |
| 6,114,135 A | 9/2000 | Goldstein | |
| 6,136,271 A | 10/2000 | Lorincz et al. | |
| 6,413,784 B1 | 7/2002 | Lundsgaard et al. | |
| 6,417,004 B1 | 7/2002 | Brady et al. | |
| 6,861,954 B2 | 3/2005 | Levin | |
| 8,372,343 B2 | 2/2013 | Goldstein | |
| 8,921,115 B2 | 12/2014 | Yuan et al. | |
| 9,857,383 B2 | 1/2018 | Goldstein | |
| 2003/0072676 A1 | 4/2003 | Fletcher-Haynes et al. | |
| 2006/0030049 A1 | 2/2006 | Bhimani et al. | |
| 2006/0147992 A1 | 7/2006 | Smith et al. | |
| 2008/0160500 A1 | 7/2008 | Fueller et al. | |
| 2008/0206880 A9 | 8/2008 | Clague et al. | |
| 2012/0329082 A1 | 12/2012 | Viola et al. | |
| 2014/0236494 A1* | 8/2014 | Kolandaivelu | G01N 33/4905 702/19 |
| 2016/0091483 A1* | 3/2016 | McCluskey | G01N 33/4905 436/69 |
| 2016/0091517 A1* | 3/2016 | Gorin | G01N 33/86 435/287.1 |
| 2019/0033221 A1* | 1/2019 | Zhang | G01N 33/86 |

FOREIGN PATENT DOCUMENTS

| | | |
|---|---|---|
| EP | 1162457 A2 | 12/2001 |
| EP | 0668926 B1 | 6/2004 |
| JP | 2011506933 A | 3/2011 |
| WO | WO 1989/010788 A1 | 11/1989 |
| WO | WO 1991/001383 A1 | 2/1991 |
| WO | WO 1991/016453 A1 | 10/1991 |
| WO | WO 1999/067646 A1 | 12/1999 |
| WO | WO 2001/082793 A2 | 11/2001 |
| WO | WO 2003/026724 A1 | 4/2003 |
| WO | WO 2003/083489 A1 | 10/2003 |
| WO | WO 2006/020773 A2 | 2/2006 |
| WO | WO 2009/073851 A1 | 6/2009 |

OTHER PUBLICATIONS

Bonser et al., "A Brain Extract as a Substitute for Platelet Suspensions in the Thromboplastin Generation Test," Nature, 1954, 174(4436):880-881.

Chadd et al., "Hypothermia and Coagulation Defects in the Newborn," Arch Dis Child, 1972, 47:819-821.

Chediak et al., "Platelet Function and Immunologic Parameters in von Willebrand's Disease Following Cryoprecipitate and Factor VIII Concentrate Infusion," The American Journal of Medicine, 1977, 62:369-375.

Cohen, "Cold Injury in Early Infancy," Israel J. Med. Sci., 1977, 13(4):405-409.

Despotis et al., "Factors Associated with Excessive Postoperative Blood Loss and Hemostatic Transfusion Requirements: A Multivariate Analysis in Cardiac Surgical Patients," Anesth Analg, 1996, 82:13-21.

Despotis et al., "On-site Prothrombin Time, Activated Partial Thromboplastin Time, and Platelet Count," Anesthesiology, 1994, 80(2):338-351.

Despotis et al., "Prospective evaluation and clinical utility of on-site monitoring of coagulation in patients undergoing cardiac operation," J Thorac Cardiovasc Surg, 1994, 107:271-9.

Despotis et al., "The Impact of Heparin Concentration and Activated Clotting Time Monitoring on Blood Conservation," J Thorac Cardiovasc Surg, 1995, 110:46-54.

Dorman et al., "Identification of Patients at Risk for Excessive Blood Loss During Coronary Artery Bypass Surgery: Thromboelastograph Versus Coagulation Screen," Anesth Analg, 1993, 76:694-700.

Easterbrook et al., "Thrombocytopenia in hypothermia: a common but poorly recognised complication," British Medical Journal, 1985, 291:23.

Essell et al., "Comparison of Thromboelastography to Bleeding Time and Standard Coagulation Tests in Patients After Cardiopulmonary Bypass," J Cardiothorac Vasc Anesth, 1993, 7(4):410-5.

Goodnough et al., "On the Need for Improved Transfusion Indicators in Cardiac Surgery," Ann Thorac Surg, 1995, 60:472-80.

Gravlee et al., "Predictive Value of Blood Clotting Tests in Cardiac Surgical Patients," Ann Thorac Surg, 1994, 58:216-21.

Hattersley, "The Treatment of Classical Hemophilia With Cryoprecipitates," JAMA, 1966, 198(3):243-247.

Hoffman et al., "Fibrinogen content of low-volume cryoprecipitate," Transfusion, 1987, 27(4):356-358.

Janson et al., "Treatment of the Bleeding Tendency in Uremia with Cryoprecipitate," The New England Journal of Medicine, 1980, 303(23):1318-1322.

Jobes et al., "Increased Accuracy and Precision of Heparin and Protamine Dosing Reduces Blood Loss and Transfusion in Patients Undergoing Primary Cardiac Operations," J Thorac Cardiovasc Surg, 1995, 110:36-45.

Johansson et al., "The Effect of Heparin and -Aminocaproic Acid on the Coagulation in Hypothermic Dogs," Acta Physiol Scand, 1964, 60:267-277.

Langdell et al., "Effect of Antihemophilic Factor on One-Stage Clotting Tests," J Lab Clin Med, 1953, 41(4):637-47.

Proctor et al., "The Partial Thromboplastin Time with Kaolin," The American Journal of Clinical Pathology, 1961, 36(3):212-19.

Ratnoff et al., "Hypothermia," Disorders of Hemostasis, 1996, Chapter 9, Disseminated Intravascular Coagulation, pp. 307.

Smiley et al., "Studies on the Prolonged Bleeding Time in Von Willebrand's Disease," Thrombosis Research, 1989, 53:417-426.

Smith, "Limit(ation)s for ACT," Anesth Analg, 1989, 142-44.

Spiess et al., "Thromboelastography as an Indicator of Post-Cardiopulmonary Bypass Coagulopathies," J Clin Monit, 1987, 3:25-30.

Tuman et al., "Comparison of Viscoelastic Measures of Coagulation after Cardiopulmonary Bypass," Anesth Analg, 1989, 69:69-75.

Wang et al., "Thromboelastogram Fails to Predict Postoperative Hemorrhage in Cardiac Patients," Ann Thorac Surg, 1992, 53:435-9.

International Search Report and Written Opinion for Application No. PCT/US2019/022558 dated May 24, 2019 (15 pages).

* cited by examiner

COAGULATION TEST DEVICE, SYSTEM, AND METHOD OF USE

BACKGROUND

Most existing coagulation tests, both point-of-care (POC) and laboratory based, diagnose bleeding abnormalities, but provide insufficient information regarding the underlying cause of bleeding. Current management of bleeding patients often includes use of "Massive Transfusion Protocols" (MTP). This protocol-guided strategy manages all patients with a one-size fit all approach and without consideration of underlying etiologies of coagulopathy in each individual patient. Laboratory tests for factor levels or visco-elastic tests require time and skilled technical staff to execute.

SUMMARY

The coagulation test device described herein requires little-to-no laboratory skills to operate and presents individualized, evidence-based results, which may aide in treatment decisions within 15 minutes from inserting the sample tube to obtaining results. Furthermore, there have been reported cases of treatment selection and administration, which have led to thromboembolic events. The device allows for the in-vitro testing of potential therapeutic agents, which can aid in determining the underlying cause of coagulopathy, and guard against the administration of agents that may induce thromboembolic events.

The coagulation test device described herein is an in vitro diagnostic point-of-care device for measuring clotting time and clot characteristics of a whole blood sample under different hemostatic conditions. Results of the test are used as an aid in management of patients with coagulopathy of unknown etiology in order to help the physician determine appropriate clinical action to arrest bleeding. Additionally, the device addresses a key problem in perioperative medicine and solves this problem by testing the effect of specific hemostatic therapeutic agents on whole blood clotting time in a bleeding patient.

In the existing state of clinical practice abnormal test results are typically addressed with an experience-based educated guess on the course of therapy to administer. The coagulation test device described herein provides personalized, clinical guidance to physicians regarding etiology of the patient's specific coagulopathy. The device simultaneously compares the effect of several hemostatic agents on whole blood clotting time and derives the underlying etiology, based on the measured responses across these hemostatic agents.

In one embodiment, a device is disclosed herein for processing a cartridge containing a whole blood sample. The device comprises a recess for receiving the cartridge, a vacuum source coupled to the cartridge, an actuator linked to the cartridge to agitate the cartridge; and a controller. The controller is configured to activate the vacuum source to move the whole blood sample from a container into a plurality of channels in the cartridge and subsequently into a plurality of reagent chambers where the blood mixes with a reagent, and then through a plurality of serpentine-shaped channels to a plurality of test chambers, activate the actuator to agitate the cartridge, receive signals from a plurality of sensors, each sensor associated with one of the test chambers, where the signals are based on the presence of a spherical member within a magnetic field generated by a magnet positioned adjacent to each of the test chambers, determine whether coagulopathy is present in the whole blood for each test chamber, and output an indicator whether coagulopathy is present in the whole blood for each test chamber on a display.

In another embodiment, a system is disclosed herein comprising a cartridge comprising a whole blood sample, the cartridge including a plurality of test chambers and a metal sphere in each test chamber and a device configured to receive the cartridge. The device includes a plurality of sensors, each sensor positioned adjacent to one of the test chambers, and a controller with the controller configured to activate a vacuum source to move a portion of the whole blood sample into each of the test chambers, move the cartridge, receive signals from each of the sensors while the cartridge is moving, determine whether the metal sphere is moving in the test chamber, determine whether the whole blood sample in each test chamber exhibits coagulopathy, and output an indicator whether coagulopathy is present in the whole blood for each test chamber on a display.

In a further embodiment, disclosed herein is a method of determining clotting characteristics of a whole blood sample. The method comprises introducing the whole blood sample into a cartridge having a plurality of test channels, wherein each test channel includes a reagent chamber, a test chamber, and a metal sphere in each test chamber; mixing the whole blood sample with a reagent in each of the reagent chambers; agitating the cartridge; detecting movement of the metal sphere in each of the test chambers with two sensors positioned adjacent to each of the test chambers; determining, with a controller, one or more clot characteristics of the whole blood sample based on detection of movement of the metal sphere; and generating an indicator of the clot characteristic for display to a user.

Other aspects of the invention will become apparent by consideration of the detailed description and accompanying drawings.

DETAILED DESCRIPTION

Figure 1:
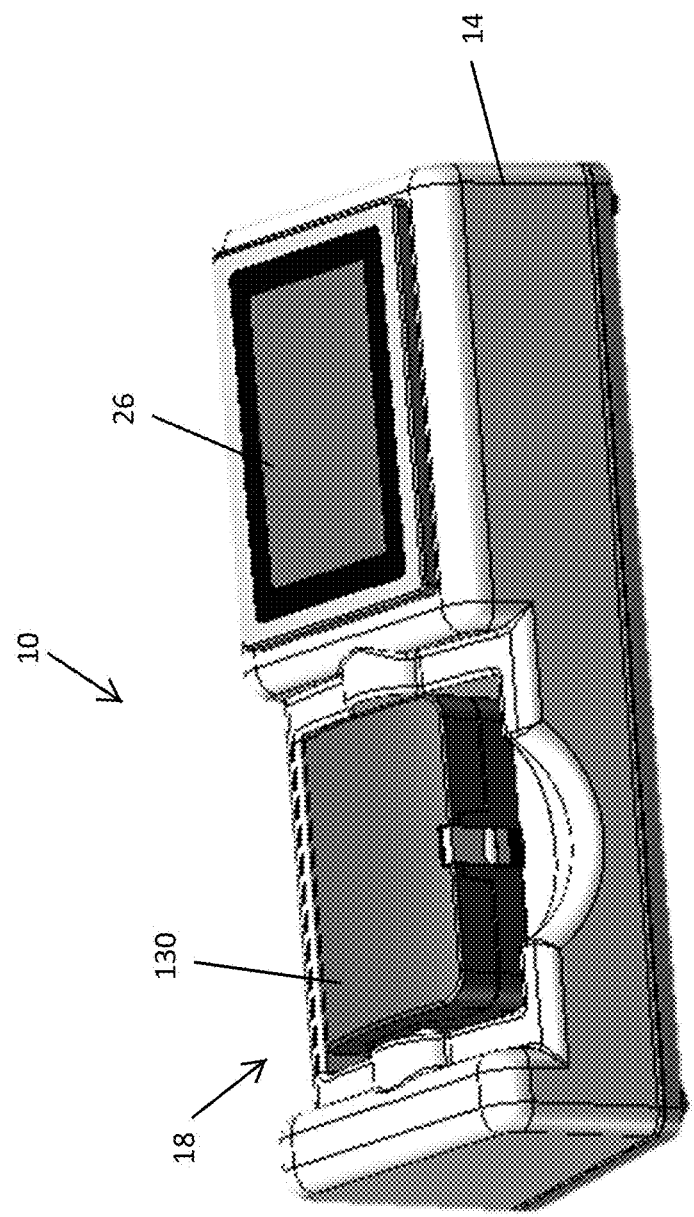
FIG. 1 is a perspective view of a coagulation test device according to an embodiment.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), SIM card, register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions. Articles "a" and "an" are used herein to refer to one or to more than one (at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

Embodiments are described herein with reference to flowchart illustrations and/or block diagrams and/or figures. The flowchart, block diagrams and other illustrations in the present disclosure illustrate the architecture, functionality, and operation of possible implementations of systems, methods, computer program products (non-transitory computer-readable medium storing instructions executable one electronic processors, such as a microprocessor, to perform a set of functions), and the like according to various embodiments of the present invention. In this regard, each block in the flowchart or block diagram(s), or accompanying figures herein may represent a module, segment, or portion of instructions, which comprises one or more executable instructions for implementing the specified logical function(s). In some alternative implementations, the functions noted in the blocks or figures may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration and/or figures and combinations of blocks in the block diagrams and/or flowchart illustration and/or figures can be implemented by special purpose hardware-based systems that perform the specified functions or acts or carry out combinations of special purpose hardware and computer instructions.

Herein, various terms that are well understood by those of ordinary skill in the art are used. The intended meaning of these terms does not depart from the accepted meaning.

The terms anti-coagulant or anti-coagulating agent may be used interchangeably, and refer to compositions that are added to, or are present in biological specimens which inhibit natural or artificial coagulation, prolonging coagulation time. Examples of anti-coagulants include, but are not limited to, sodium citrate, hirudin, chelating agents, exemplified by ethylenediamine tetraacetic acid (EDTA), diethylenetriamine pentaacetic acid (DTPA), 1,2-diaminocyclohexane tetraacetic acid (DCTA), ethylenebis (oxyethylenenitrilo) tetraacetic acid (EGTA), or by complexing agents, such as heparin, and heparin species, such as heparin Sulfate and low-molecular weight heparins, as well as coumarins and indandiones, factor Xa inhibitors, and thrombin inhibitors.

The term coagulopathy as used herein refers to any bleeding disorder that affects the way a patient's blood clots. The term hyper-coagulable as used herein refers to a state of abnormal increase towards blood clot formation. The term hypo-coagulable as used herein refers to a state of abnormal decrease away from blood clot formation.

Examples of excitation sources as used herein may be magnetic fields, electromagnetic fields, light, or ultrasonic energy. Excitation sensors as used herein are means capable of detecting the presence, absence, or changes in excitation source as affected or disrupted by the test element in the test sample.

The term blood clot lysis and fibrinolysis may be used interchangeably and as used herein refers to the breakdown of fibrin, usually by the enzymatic action of plasmin. The term clot integrity and clot strength may be used interchangeably and as used herein refers to the strength of a clot that has formed as a result of a fibrin and platelets mesh. The term premature thrombolysis as used herein refers to the premature dissolution of a clot after formation and is indicative of a defect in hemostasis.

Figure 2:
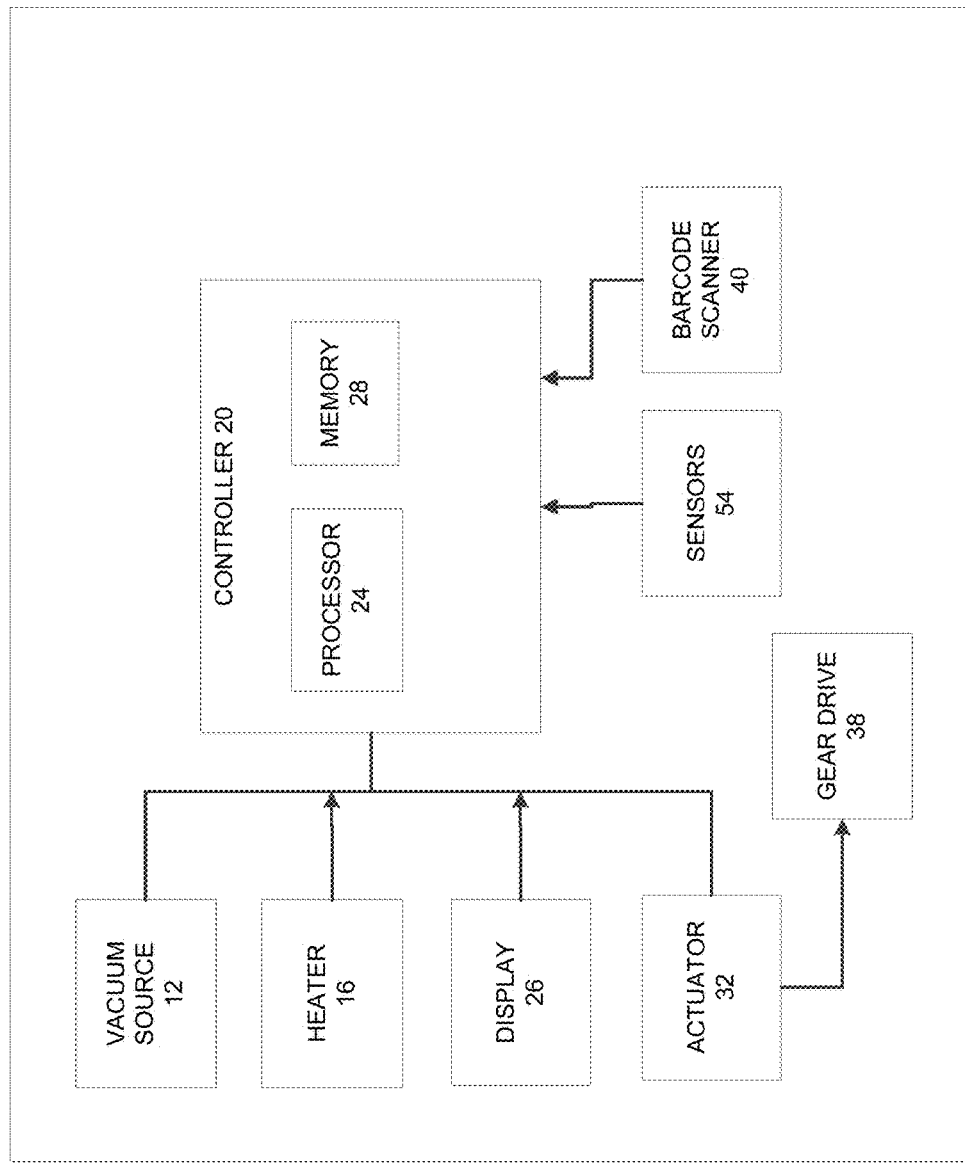
FIG. 2 is a block diagram of the coagulation test device shown in FIG. 1.

FIGS. 1-2 illustrate a coagulation test device 10 according to some embodiments. The coagulation test device 10 provides the ability to simultaneously evaluate clotting time and determine clot characteristics of whole blood under multiple hemostatic conditions according to some embodiments. As illustrated in FIG. 1, the coagulation test device 10 includes a housing 14, a recessed area 18 configured to receive a cartridge 30, and a display 26. As shown, the recessed area 18 and the display 26 are positioned adjacent to one another in the housing 14; however other configurations and orientations between the recessed area 18 and display 26 are possible.

With reference to FIG. 2, the coagulation test device 10 also includes a vacuum source 12 supported by the housing 14 and a heater 16 supported by the housing 14. The coagulation test device 10 further includes a controller 20 including an electronic processor 24 and a computer-readable, non-transitory memory 28. The memory 28 stores instructions that are executed by the electronic processor 24 to provide the functionality of the controller 20 as discussed herein. The controller 20 is also coupled to the display 26 and is configured to output graphical information and data. For example, in some implementations, the device 10 is configured to output on the display 26 specific data related to hemostatic reagents under test and whole blood clotting time for each channel while the test is in progress. Hemostatic agents may include fibrinogen, Factor VIII, Factor IX, cryoprecipitate, human plasma, Factor VIII and von Willebrand, 3 factor Prothrombin Complex Concentrate (PCC), 4 factor Prothrombin Complex Concentrate (PCC), Protamine Sulfate, platelets, Heparinase, Factor VII, Factor VIIa, and Factor XIII, however other suitable hemostatic agents may be employed. When the test is completed, the display 26 also can display a diagnosis and other testing characteristics derived from analysis of the test channel data. The controller 20 is also coupled to the vacuum source 12 and the heater 16 to control activation and deactivation.

Figure 3:
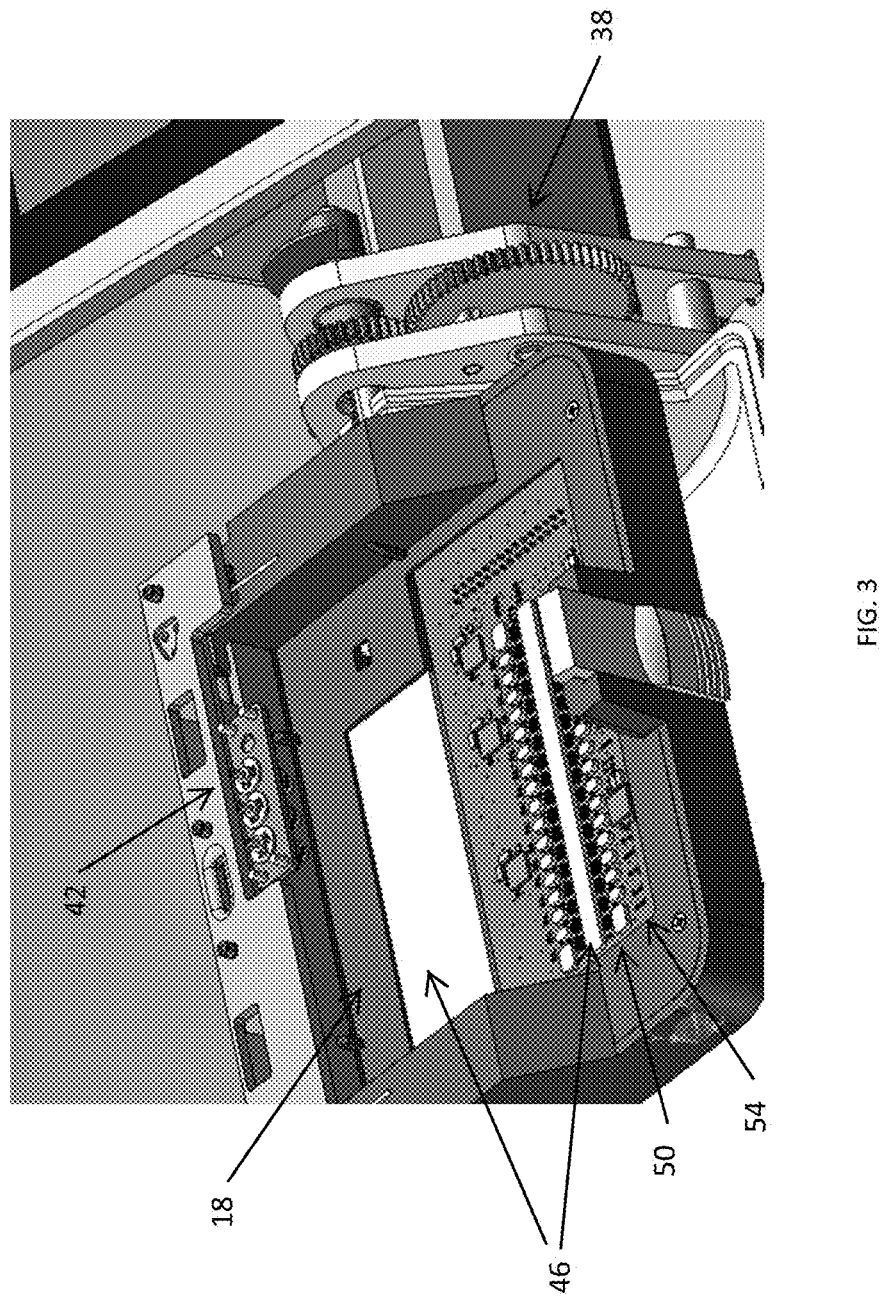
FIG. 3 is a perspective view of the coagulation test device shown in FIG. 1 with a test cartridge and protective cover removed.
Figure 4:
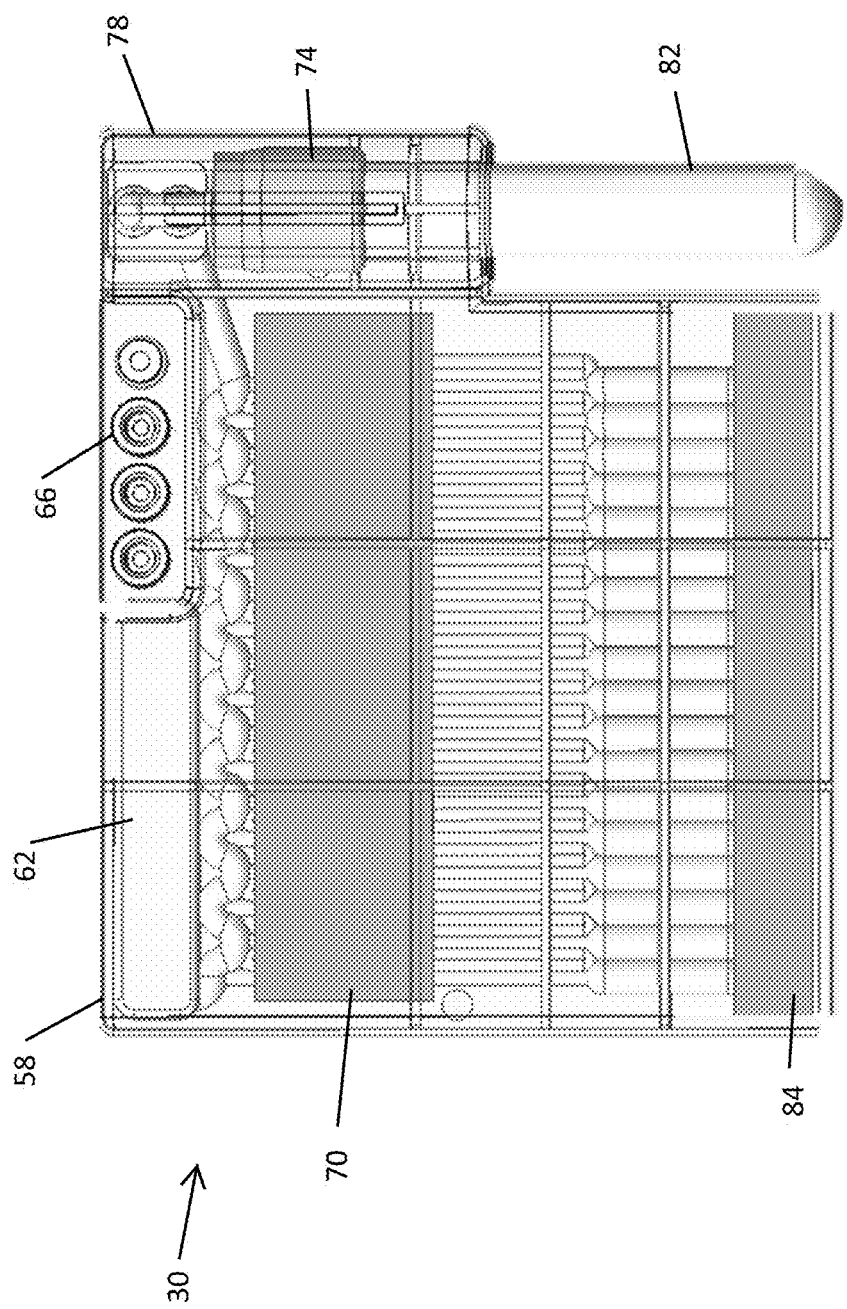
FIG. 4 is a perspective top view of a test cartridge with inserted sample tube used with the coagulation test device shown in FIG. 1.

With reference to FIG. 3, the recessed area 18 is configured to receive the cartridge 30, which allows for up to 18 channels of clotting time testing in a single cartridge 30. In one configuration, the cartridge 30 is about the size of a microtiter plate (e.g., 9.7 mm by 11.8 mm) and conducts 18 individual coagulation tests. Additional or fewer channels may be utilized within the envelope of the cartridge 30. For example, for purposes of illustration, FIGS. 4-5B show 18 channels in the cartridge 30, however the cartridge 30 may include more or fewer than 18 channels. In one embodiment, the device 10 accepts a sample tube containing 4.5 ml of whole blood. For 18 channels of coagulation testing, this embodiment creates 18 aliquots of approximately 150 microliters for testing. The construction and dimensions of the cartridge 30 may be altered to reduce the sample volume to 2.7 ml by reducing the size of the reagent chambers and subsequent test chambers.

With continued reference to FIG. 3, the recessed area 18 is mechanically linked to a gear drive 38 for agitating the cartridge 30 and samples therein. The gear drive 38 is in communication with the controller 20 via an actuator 32 (e.g., motor, pump, etc.). In one example, the actuator provides an agitation/rocking speed between 90 degrees and 180 degrees per second with a rocking angle between 10 degrees and 75 degrees. One cycle duration is between 1 and 5 seconds. In other examples, the actuator can provide a suitable rocking speed and rocking angle that may be less than or greater than the parameters provided herein. Similarly, the cycle duration can be suitably adjusted within the scope of the operation of the device 10.

The recessed area 18 also includes one or more vacuum ports 42 that interface with the cartridge 30, one or more heater regions 46 for incubation and test regions, a plurality of magnets 50, and a plurality of sensors 54 in communication with the controller 20.

FIG. 4 illustrates an embodiment of the cartridge 30. The cartridge 30 includes a housing 58, a waste collection area 62, and one or more vacuum ports 66 configured to interface with the one or more vacuum ports 42 on the recessed area 18. The cartridge 30 also includes a reagent vacuum region 70, a sample tube interface 74, a sample tube housing 78 configured to receive a sample tube 82 (as shown in the sample tube housing 78 in FIG. 4), and a test channel vacuum region 84.

The cartridge 30 is designed for injection molding and secondary assembly operations. The cartridge 30 is sealed with a film that is compatible with blood and does not influence coagulation. The cartridge 30 includes a plurality of chambers that are isolated from each other. The blood sample is introduced into the cartridge 30 by the vacuum source 12. Hydrophobic filters 34 (FIG. 5B) are used to stop the flow of blood when it has been fully aspirated. The vacuum ports 66 are at atmospheric pressure when the cartridge 30 is outside of the device 10. Since no pressure is being applied to the sample, the sample remains in the sample tube 82 until it is loaded onto the device 10 and the sample sequence has begun.

The cartridge 30 includes a common feed channel X (shown in FIG. 5A) that connects the sample input to the chambers containing the individual hemostatic reagents. Each reagent chamber is connected to one of the vacuum ports 66 through a series of hydrophobic filters 34 for each channel. As the sample is aspirated into the cartridge 30, each channel is filled sequentially at a rate established by a predetermined vacuum pressure of the vacuum source 12. When an individual channel is filled completely, the hydrophobic filter 34 shown in FIG. 5B for that channel is blocked and the channel stops filling beyond its capacity. The remaining channels fill until each of the filters are blocked. The controller 20 monitors duration of applied vacuum and may also monitor the pressure drop across the filters to determine when all of the channels are filled.

Figure 5A:
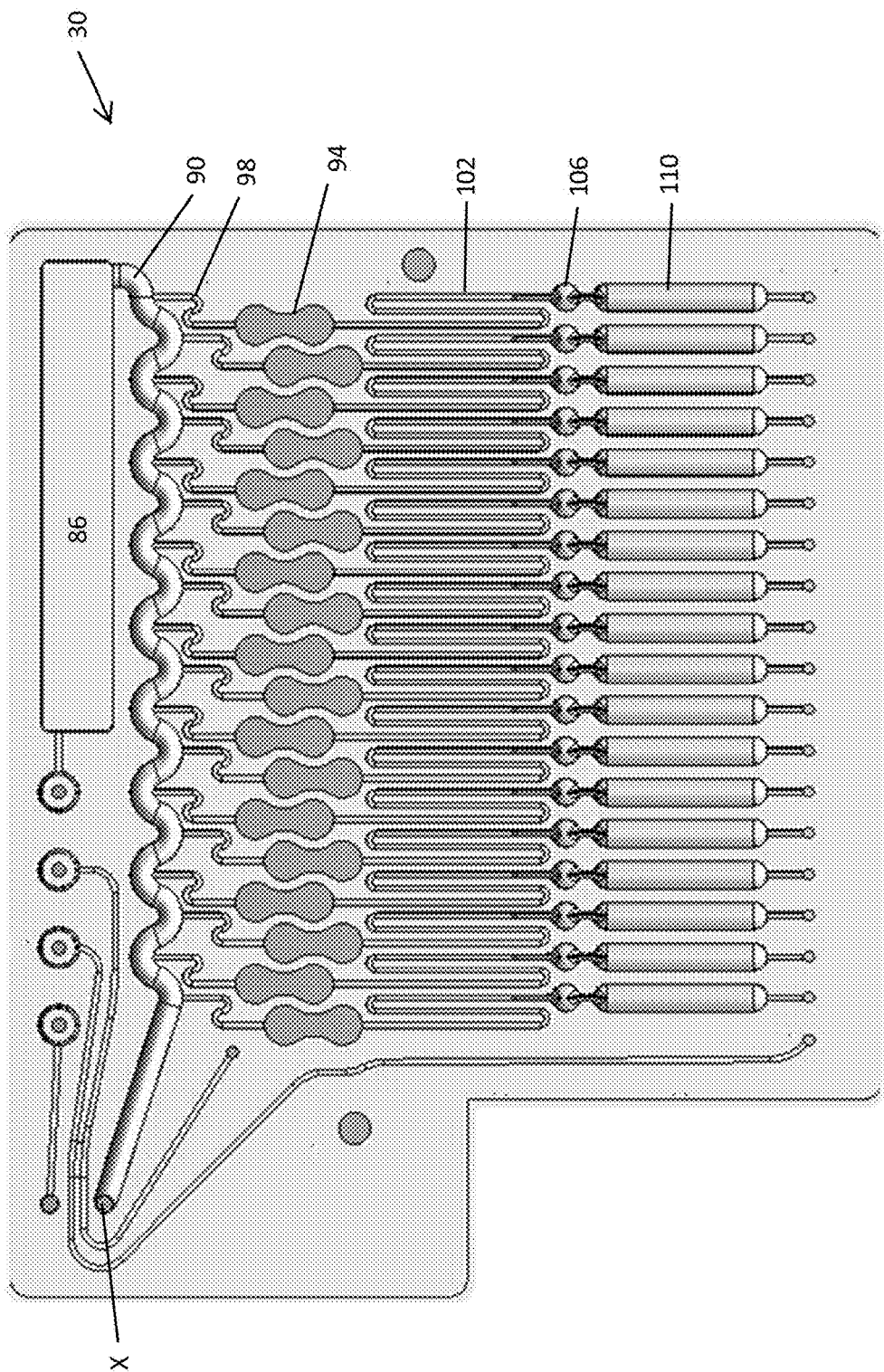
FIG. 5A is a perspective view of fluidics pathways of the test cartridge shown in FIG. 4.
Figure 5B:
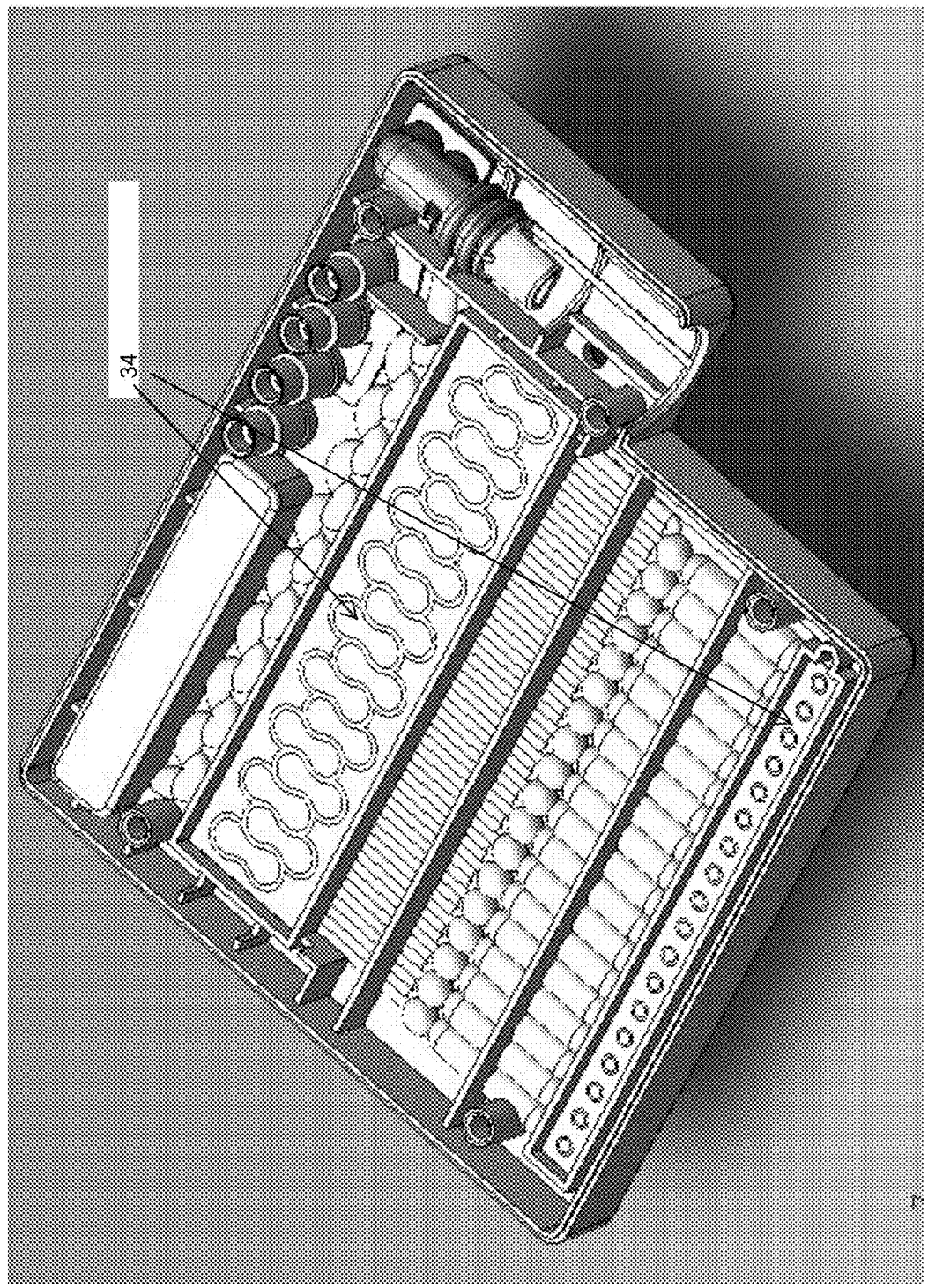
FIG. 5B is a rear perspective view of the test cartridge shown in FIG. 4 and showing hydrophobic membranes.

The fluidics of the cartridge 30 are further described and illustrated in FIGS. 5A-B according to some embodiments. The cartridge 30 includes a waste region 86, a sample feed channel 90 in communication with the waste region 86, and one or more hemostatic reagent chambers 94 in communication with the sample feed channel 90 via respective channels 98. The cartridge 30 also includes one or more serpentine mixing channels 102 at an outlet of a respective hemostatic reagent chamber 94. The serpentine mixing channels 102 are in fluid communication with one or more anticoagulant reversal chambers 106 (for if an anti-coagulant was used to anti-coagulate the whole blood sample), respectively, which are each then in respective communication with one or more clotting test chambers 110. As noted above, and as illustrated herein, the cartridge 30 is shown with 18 individual test channels 112, with each channel including a reagent chamber 94, a serpentine fluid path 102, and a test chamber 110, however, the cartridge 30 may include more or fewer than 18 test channels 112 in other constructions.

Figure 6:
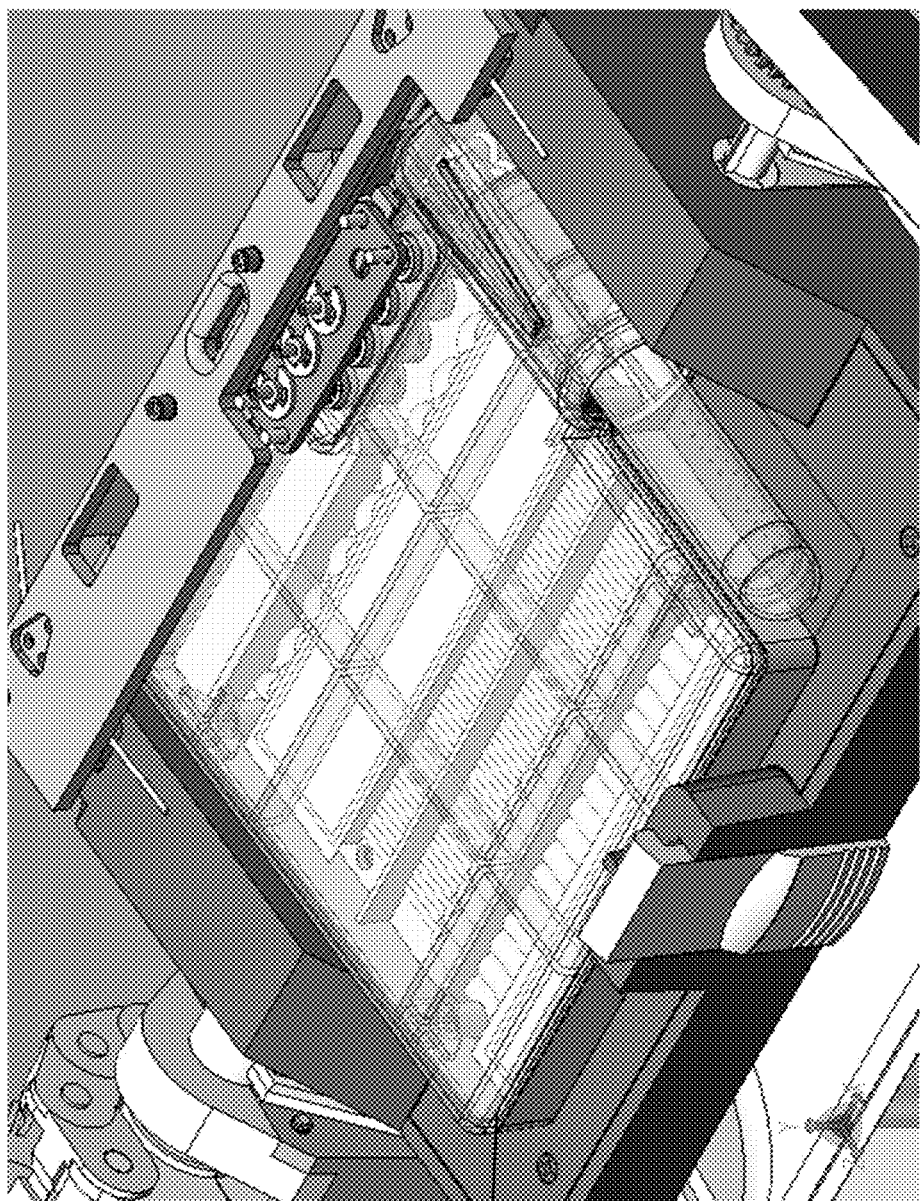
FIG. 6 is a perspective view of the coagulation test device with the test cartridge in place prior to testing.

FIG. 6 illustrates a system for determining clotting characteristics of a whole blood sample 100 including the device 10 and the cartridge 30. In particular, the cartridge 30 is shown in position in the recessed area 18 of the device 10. The vacuum ports 42 in the recessed area 18 are in communication with the vacuum ports 66 on the cartridge 30.

Figure 7:
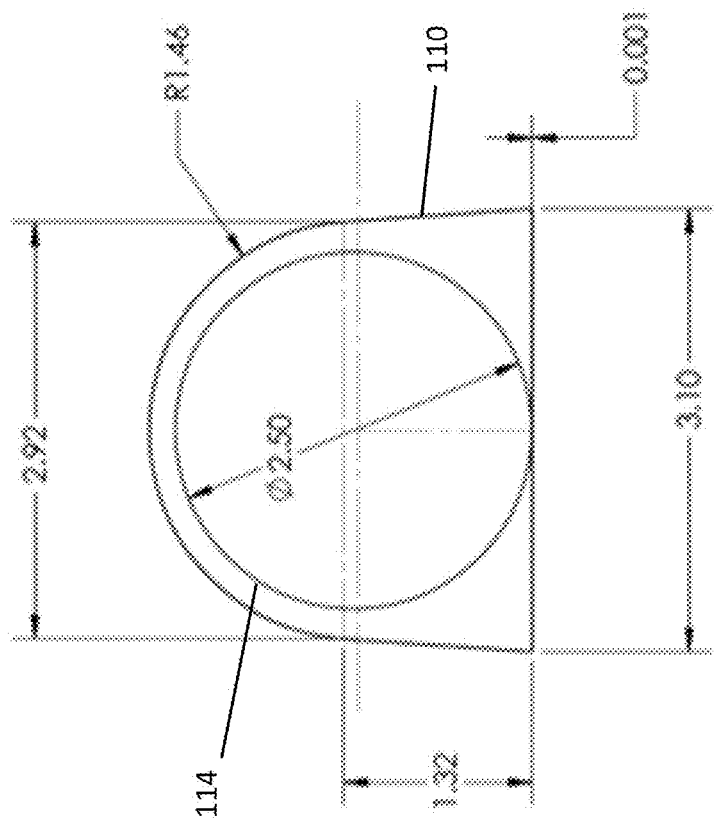
FIG. 7 is an enlarged cross-sectional view of a test chamber and a spherical member in the test cartridge shown in FIG. 4.

Clot formation in whole blood or plasma can be measured in many different ways. Electrical conductivity requires contact with the whole blood. Capacitive measurements do not require contact and can be measured through barrier films; however, these techniques require some type of electrical connection to the testing device in order to bring signals in and out of the device. The coagulation test device 10 described herein utilizes a non-contact measurement method where a sphere 114, comprised of a magnetic material, is within each of the 18 test chambers 110 and is used to determine the viscosity of the whole blood in each test chamber 110. FIG. 7 illustrates a cross-section of an enlarged test chamber 110 and the spherical member 114 positioned therein. Agitating the test chamber 110 causes the spherical members 114 to roll through the whole blood in each test chamber 110. The sensors 54 are positioned in close proximity to the test chamber 110 to measure the presence of the spherical member 114 in the test chamber 110 as it is agitated by the device 10. In one construction, the test chambers 110 have a width of 3.0 mm and a length of 18 mm to accommodate a sample aliquot volume of approximately 150 microliters. In other constructions, the test chambers 110 could have a width of 1.5 mm and a length of 10 mm in order to reduce the sample aliquot volume to approximately 70 microliters. In one example construction, the test chambers 110 are spaced 4.5 mm apart which allows for 18 channels of clotting time testing to be incorporated into the envelope of the cartridge 30. Other suitable dimensions are possible within the scope of the device described herein.

Sensing travel speed within a test chamber 110 is accomplished by measuring the change in magnetic flux as the spherical member 114 passes in proximity to the sensors 54 located along the path of each test chamber 110. The sensor 54 does not require contact with the test chamber 110 and can be spaced up to 0.8 mm away from the test chamber surface. The sensors 54 sense the signals generated within the housing 58 of the cartridge 30 from their respective test chamber 110. This non-contact method of measurement enables complete separation between the cartridge 30 and the device 10, thereby eliminating the need for the device 10 to make contact with the whole blood sample. This configuration also eliminates any device cleaning or maintenance steps between test samples. It further eliminates the possibility of the device losing functionality due to a clot in the device fluid pathways.

Figure 9:
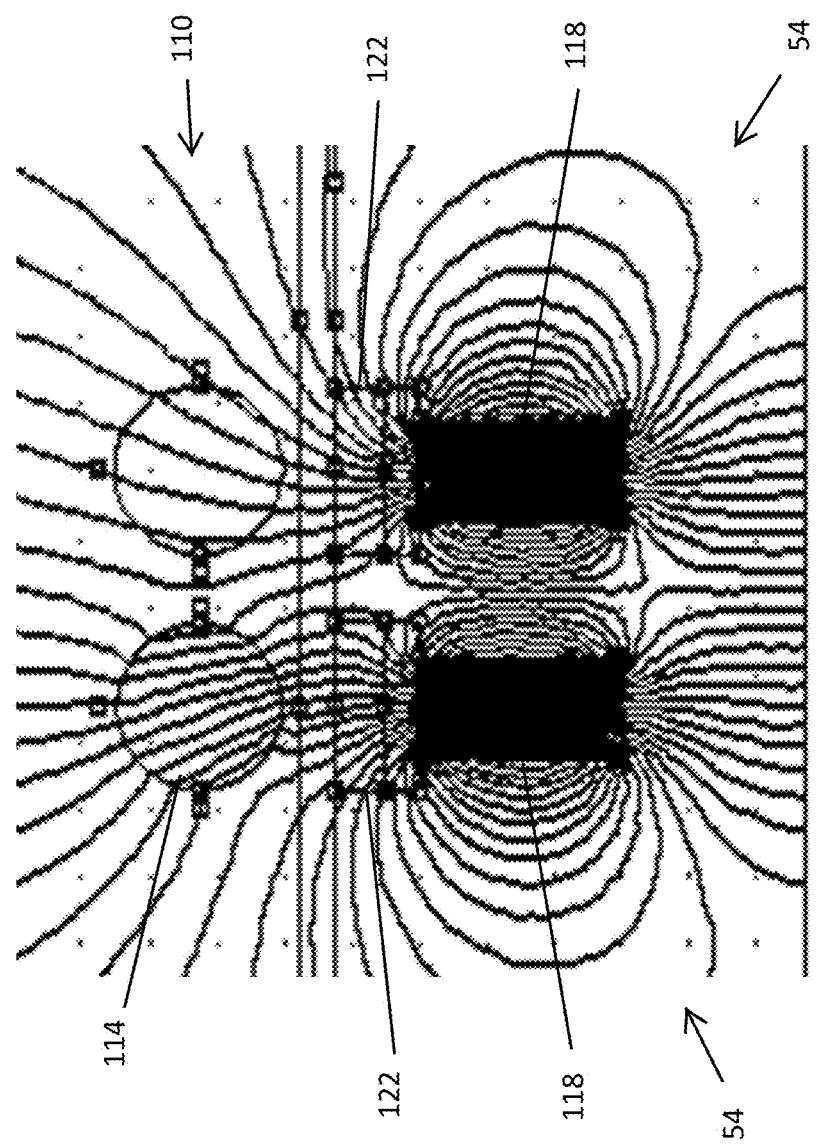
FIG. 9 illustrates a difference in magnetic field line map.
Figure 10:
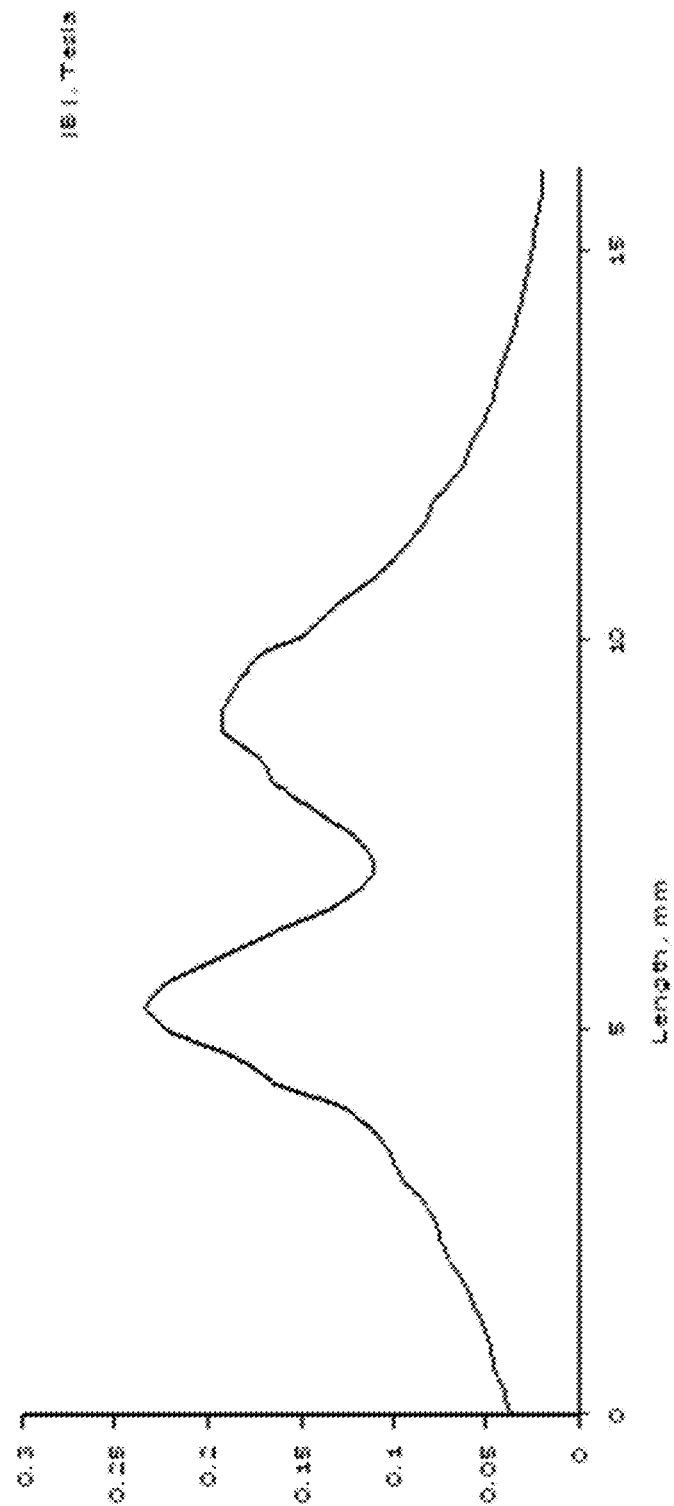
FIG. 10 graphically illustrates sensor detection of a spherical member within the test chamber.

Each test chamber 110 is associated with two sensors 54, located linearly along the travel path of the spherical member 114 in the test chamber spaced apart by a distance (e.g., 9.5 mm). With reference to FIG. 9, each sensor 54 is comprised of a magnetic member 118 (e.g., comprised of one or more rare earth metals) of sufficient magnetic field strength whereby the magnetic field extends into the test chamber region, and a Hall-Effect sensor 122, which is located between the magnetic member 118 and the test chamber 110. The Hall-Effect sensors 122 produce a voltage signal proportional to the magnetic field of between 8 and 10 millivolts per gauss. The controller 20 records a baseline, quiescent reading of the magnetic field for each sensor 54 at the beginning of an agitation cycle. This baseline measurement is used to establish the amount of disturbance of the field as the spherical member 114 passes over the sensors 54. As the spherical member 114 passes over the sensors 54, the spherical member 114 causes a disturbance in the quiescent magnetic field and is detected by the sensor 54. This disturbance in magnetic flux is detected by the Hall-Effect sensor 122 and converted to a voltage. The voltage signal for each sensor 54 is then transmitted to the controller 20. A signal threshold is established to remove signal artifacts. The voltage signal form the sensor 54 can be converted to a digital signal via a series of analog to digital converters. Since there are two sensors 54 located for each test chamber 110, the time between the peak of the disturbances of the two sensors 54 relates directly to the travel time of the spherical member 114 within the test chamber 110. By this method, the viscosity of the fluid in the test chamber 110 can be traced as the device 10 agitates the test chamber 110 over a period of time, causing the spherical member 114 to pass by the sensors 54. FIG. 9 illustrates a magnetic field map showing the interaction with the test chamber 110 and the spherical member 114. As shown in FIG. 9, the map on the left shows how the spherical member causes more field lines than the map on the right, where no spherical member is present.

Figure 13:
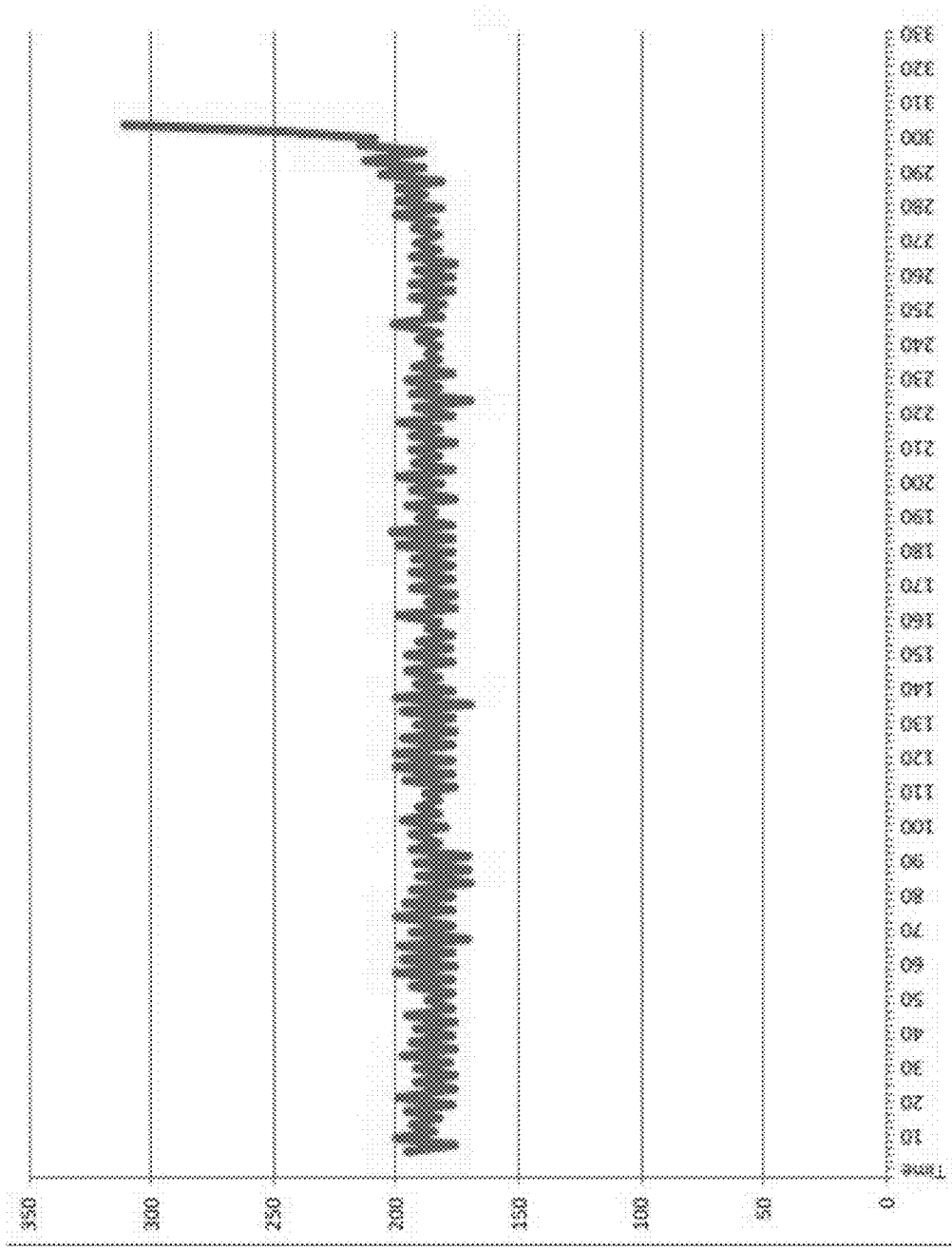
FIG. 13 graphically illustrates the sensor signals during the onset of clot formation.

The test chambers 110, sensors 54, and controller 20 determine the travel time of the spherical member 114 in each test chamber at a predetermined and programmable agitation rate. The viscosity of the fluid in each test chamber 110 is proportional to the travel time within the chamber. As such, the progression of clotting can be viewed as an increase in fluid viscosity vs. time. The coagulation cascade is truly a cascade of events and is therefore non-linear. The traces of travel time for the device 10 can detect and monitor quiescent blood status as it approaches coagulation. Shortly after this initial onset of clotting, the fluid rapidly approaches a high viscosity by forming a clot as shown in FIG. 13. The angle of trajectory from a fluid state to clot formation is also measured and used as a basis for diagnosis of apparent factor or platelet function deficiency.

Figure 14:
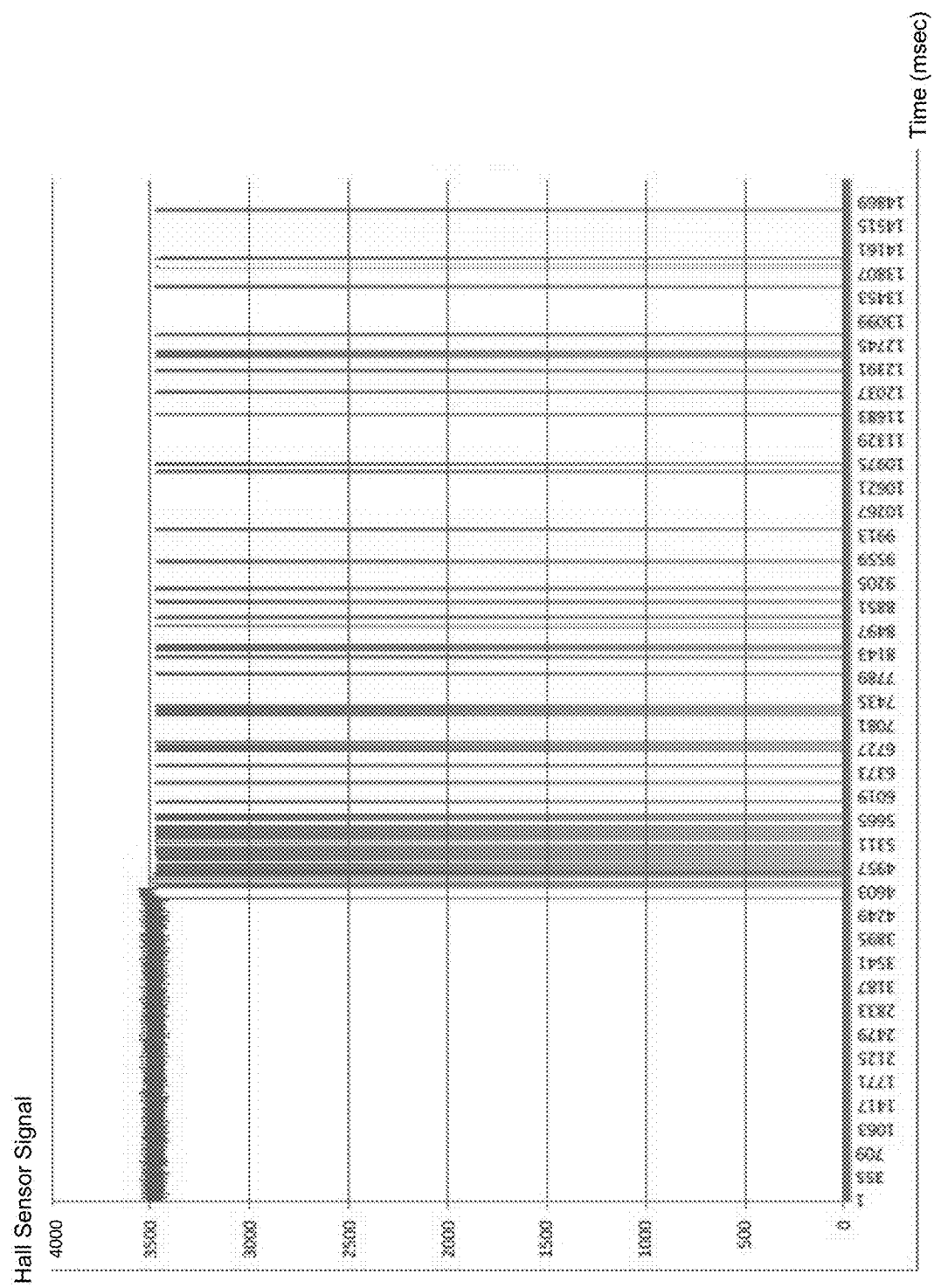
FIG. 14 graphically illustrates detection of movement of the spherical member within the test chamber when a weak clot is present in the test chamber.

In addition to clotting time, the device 10 is capable of determining the integrity or strength of the clots being formed. Each test chamber 110 within the device 10 has two independent sensors 54 (as described above), by which travel time is calculated. When the spherical member 114 fails to traverse both sensors 54 within a test chamber, a travel time cannot be calculated. This is indicative of a clot that is impeding the full travel of the spherical member 114 within a test chamber 110. However, since the gravitational forces on the spherical member 114 within a test chamber are less than 1G, it is possible for a spherical member 114 to be held by a weak clot, where the spherical member 114 will continue to move over a limited range of the full chamber length. The device 10 monitors the signals from both sensors 54 and may detect that one of the two sensors 54 is continuing to provide a signal. This signal is indicative of a weak clot that is preventing the spherical member 114 from fully traveling the length of the test chamber 110, yet is still allowing the spherical member 114 to move. As shown in FIG. 14, only one of the two sensors continues to show movement of the spherical member 114.

FIG. 14 shows a condition where the spherical member 114 is transitioning across only one of the sensors 54 with each agitation or duty cycle of the cartridge, indicating a weak clot. The frequency by which the spherical member 114 is detected by a single one of the two sensors 54 is indicative of clot integrity, where a high frequency of signal generation indicates a weak clot. As the number of single sensor signals decreases, this is indicative of increased clot strength. No movement of the spherical member 114 would indicate a strong clot after clot formation, yielding a frequency of zero or below a threshold set by the device 10. The device 10 establishes a cut-off value for clot integrity.

In one example, the duty cycle of the spherical member 114 is proportional to the integrity of the clot where the duty cycle of greater that 40% is indicative of a severely weak clot, the duty cycle of between 25% and 40% is indicative of a moderately weak clot, the duty cycle of between 10% and 25% is indicative of a moderately strong clot, and the duty cycle between 0% and 10% is indicative of a strong clot.

Figure 8:
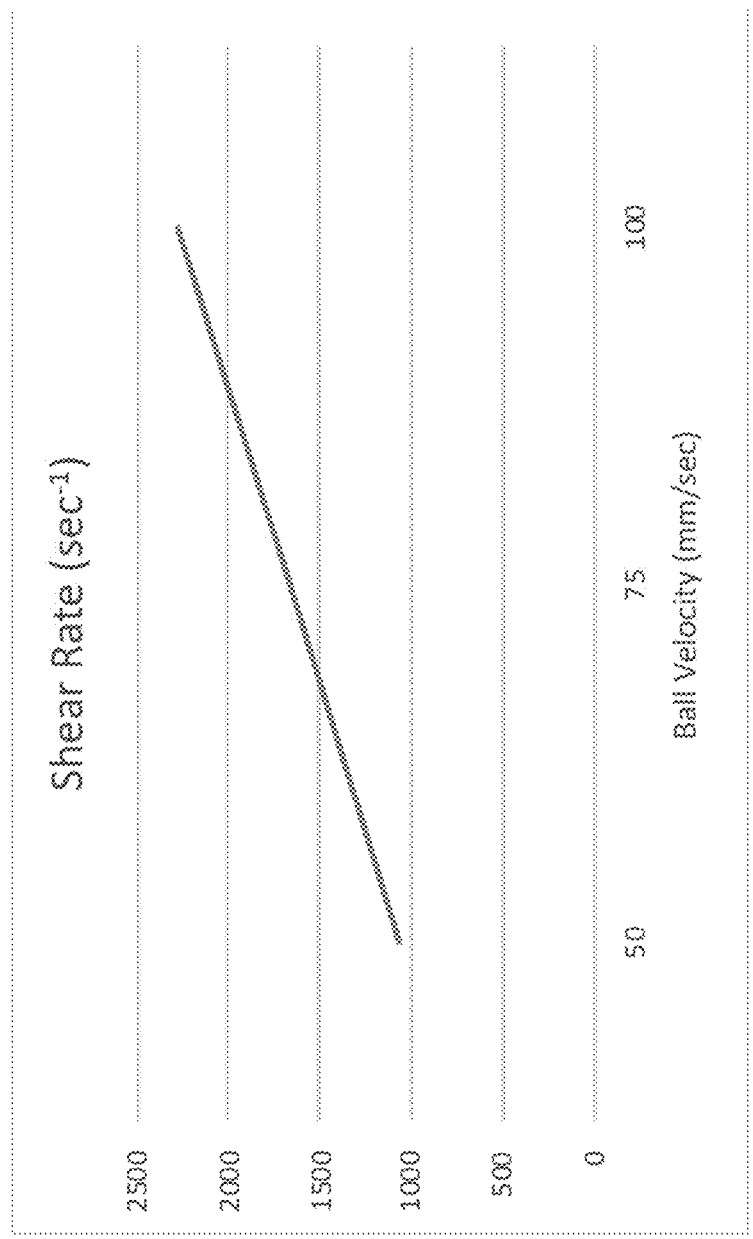
FIG. 8 graphically illustrates the relationship between travel speed of a spherical member within the test chamber and the resulting shear rate applied to the blood sample in the test chamber.

The relative size of the spherical member 114 within the test chamber and the test chamber diameter helps to induce coagulation in a manner similar to physiological clotting mechanisms. It is known that shear stress within the human vascular system promotes coagulation. Many coagulation test systems require the addition of a high surface area pro-coagulant such as Celite or Kaolin to reduce the normal clotting time to a level that meets the needs for a rapid clotting time. The method and apparatus described herein eliminates the need for pro-coagulants by inducing physiological shear rate and shear stress within each test channel of between 500 and 4,000 $sec^{-1}$ or 100 to 1,000 dynes per second. FIG. 8 illustrates the relationship between the travel speed of the spherical member 114 within the test chamber 110 and the resulting shear rate, based upon the diameter of the test chamber and the relative size of the spherical member 114 in the test chamber. The shear rate can be adjusted by altering the agitation angle, the test chamber diameter and the relative spherical member diameter. However, the system could also be used with the addition of a pro-coagulant, such as kaolin, citrate, tissue factor, phospholipid, or other appropriate activator, if a more rapid time to test results is desired.

Figure 11:
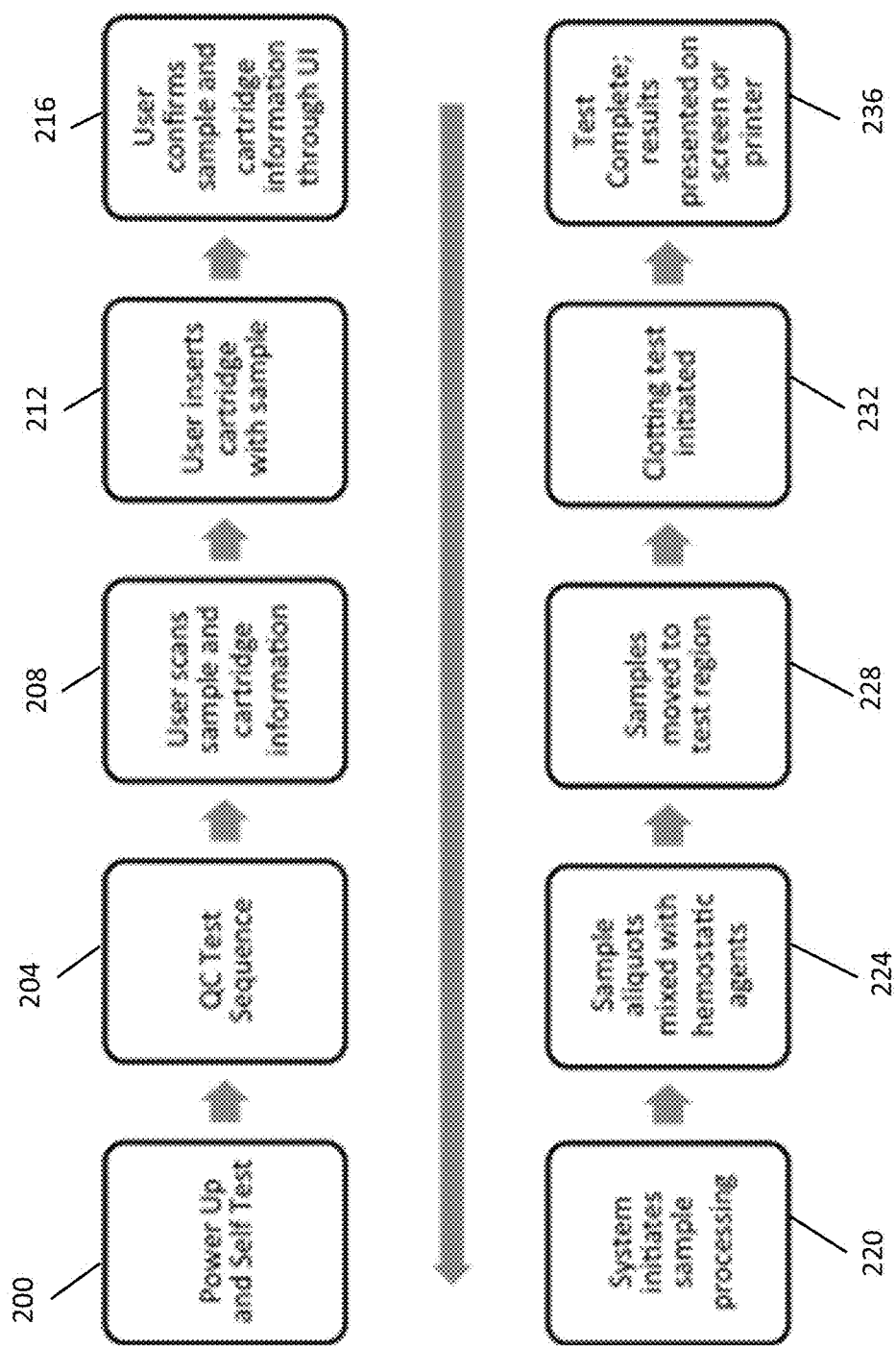
FIG. 11 is a flow chart of a method of operation of the coagulation test device illustrated in FIG. 1.

With reference to FIG. 11, sample processing begins with power up of the device 10 (at 200). The device 10 undergoes quality control tests (at 204). The device 10 performs a quality check to ensure that all electro-mechanical subsystems are in proper working order. Subsystems such as the vacuum system, the temperature elements and magnetic sensors are all checked prior to allowing a user to initiate a sample test. Additionally, the device is supplied with a re-usable QC cartridge which agitates the QC cartridge in a manner similar to a sample test to ensure that all electro-mechanical systems are working properly. The re-usable cartridge test results are recorded in the controller or memory. The QC cartridge is removed and the device is then ready to accept a patient sample. Next, the sample tube (filled with whole blood from a patient; the sample tube includes a unique barcode) is identified to the device 10 (at 208). The device 10 allows for entry of all information required to run a test with no operator typing. The device 10 can include a barcode scanner 40 in communication with the controller 20. The operator places the sample tube barcode in front of the scanner 40. The scanner 40 records the barcode and sample information into the memory 28 or other storage device (e.g., database, local or remote from device 10). The device 10 has an override function that can permit manual entry of patient information via the display 26 (e.g., touchscreen). The patient sample also must be associated with a test cartridge 30. The operator places the barcode affixed to the cartridge in front of the scanner 40. The scanner 40 records the cartridge 30 information into the memory 28 or other storage device (e.g., database, local or remote from device 10). If the sample tube does not have a barcode, then the operator can be prompted to enter the information via an on-screen keyboard on the display 26.

The sample and cartridge 30 are loaded onto the device 10 (at 212) and the operator confirms (at 216) the sample and cartridge 30 via a user interface on the display 26. A cover 130 on the device is lowered onto the recessed area 18. The cover 130 includes the vacuum connections that interface with the vacuum ports 66 on the cartridge 30 necessary for moving fluids through the cartridge 30 during sample processing and prior to initiating the clotting time tests. The vacuum ports 66 on the cartridge 30 are connected to the vacuum ports 42 in the device 10 through the action of closing the cover 130. The cover 130 also applies pressure to the cartridge 30 to maintain a uniform distance between the cartridge 30 and the sensors 54 within the device 10. The operator initiates the testing sequence via the user interface on the display 26.

Samples presented to the device 10 are typically anti-coagulated in order to allow time between sample collection and sample testing. This is a common practice for most blood testing procedures. The device 10 also can test a sample that is not anti-coagulated with a cartridge that does not contain the anti-coagulant reversal agent (e.g., calcium); however, there are time constraints for placing a non-anticoagulated sample into the cartridge 30 and onto the device 10.

The cartridge 30 is configured to receive a sample vacuum drawtube (e.g., an evacuated container with a flexible cap) as a sample input device in the sample tube housing 78. This eliminates the need for the sample to be pipetted into the cartridge 30, a process common to laboratory instruments, but not required for the device 10. The operator inserts the sample drawtube directly into the cartridge 30 (in the sample tube housing 78) and places the cartridge 30 onto the recessed area 18 in the device 10. The cartridge 30 prevents the blood sample from moving into the cartridge by controlling any vent path from being opened prior to placement on the device 10. The sample in the tube is accessed by one or more needles (e.g., two needles) that pierce the flexible cap. The operator inserts the sample tube into the sample tube receiver on the cartridge. Gentle insertion force causes the needle assembly to pierce the sample tube cap. One needle serves to aspirate the sample and the other serves as a vent to allow the blood to flow from the drawtube when the vacuum is applied.

The device 10 processes (at 220) the sample with a known set of programmed parameters. The first step is to pierce the flexible cap to draw the blood from the sample tube and fill the sample feed channel 90 and the connected reagent-containing chambers 94. The blood travels from the sample tube into the cartridge 30 at point X (shown in FIG. 5A) and fills the sample feed channel 90, and begins to fill the reagent-containing chambers 94. The controller 20 activates the vacuum source 12 in the housing 14 to apply vacuum to the blood sample in the cartridge. A pressure regulator that is in line with the vacuum pump is read by the device 10 so that the pressure is controlled to a preset value. Typical vacuum levels for sample aspiration are between 50 and 100 millibars (mb). In this sequence, the initial sample is now split into 18 equal and isolated aliquots of the blood sample.

The controller 20 selects certain valves in the vacuum ports 66 thereby controlling the direction of the vacuum. The blood sample continues to move through the various channels in the cartridge 30. The reagent chambers 94 contain individual doses of a variety of hemostatic agents. These agents are dried and remain in the reagent chamber 94 as part of the manufacturing process. Drying methods may be lyophilization or air drying, depending upon the reagent properties. The design of the cartridge is such that the blood sample is drawn into the reagent chambers 94 from the bottom of the chamber and drawn to the upper portion of the chamber by the vacuum source 12. The dried reagents are rehydrated by the entering sample volume of blood (at 224). Each reagent chamber 94 contains a hydrophobic filter, which prevents the reagent chambers from overfilling. The device 10 applies vacuum for a pre-set time duration or monitors the pressure drop across the hydrophobic filters until all filters are blocked.

Each sample-reagent complex must be separated from its nearest neighboring sample-reagent complex in order to avoid cross contamination. After filling the individual reagent chambers 94, the device 10 clears the sample feed channel 90 that connects the reagent chambers 94 by closing valves used to direct the sample to the reagent chambers 94 and opens valves to direct the sample feed channel 90 contents to the waste area 62 in the cartridge 30. An absorbent material collects the waste from the feed channel 90. Each sample aliquot is now isolated from its adjacent reagent chambers 94 by a large air gap created by the empty feed channel 90.

Coagulation is a temperature dependent phenomenon. The controller 20 activates the heater 16 to provide thermal energy (via heater region 36 on the recessed area 18) to the cartridge 30 and bring the sample aliquots within the reagent chambers 94 to a programmable temperature value of between 25 and 40 degrees Celsius with normal test temperature of 37 degrees Celsius. This range allows for testing samples under normal, hypo-thermic and hyper-thermic conditions. The sample aliquots are incubated with the hemostatic agents for a programmable period of time, typically between 1 minute and 10 minutes. In other embodiments, the sample aliquots are incubated with the hemostatic agents between 3-5 minutes. This allows the temperature of the sample aliquots to equilibrate to the proper temperature as well as allowing the hemostatic agents to fully dissolve and diffuse into the sample aliquots.

Up until this point, the blood sample and the reagents are anti-coagulated to prevent the blood sample from starting to clot until all sample aliquots are ready to be tested. Prior to initiating the clotting time test for each test channel, the anti-coagulant must be reversed. The serpentine-shaped channel 102 connects the reagent chambers 94 with the test chambers 110. The narrow diameter of the serpentine section increases the fluid velocity as it travels from the reagent region to the test region. In line with the flow of each channel is a precise amount of dried or lyophilized calcium. The traveling fluid rehydrates the calcium and mixes with the sample aliquots at the time of transfer. The cartridge 30 contains individual quantities of calcium in each channel, directly before the sample enters the test region. The calcium mixes with the aliquots as it proceeds to the test region. The anticoagulant in each aliquot has now been reversed and the clotting cascade can begin.

The controller 20 transmits a signal to change the direction of the vacuum source 12 via the valves and directs the flow of the sample aliquots from the reagent chambers 94 to the test chambers 110 (at 228). Typical vacuum levels are between 50 mb and 100 mb. The cartridge 30 and test chambers 110 are placed at a predetermined angle between 10 and 40 degrees relative to the horizontal position of the cartridge when placed on the device so as to facilitate channel filling and to minimize the possibility of trapping an air bubble in the test chambers 110. Each test chamber 110 has a hydrophobic filter in line with the vacuum source 12 to prevent over-filling of the test chamber and drawing blood into the device vacuum system.

With all (or some) of the test chambers 110 filled and the sample aliquots' anti-coagulation state reversed, the controller 20 activates the actuator 32 to begin (at 232) to agitate the cartridge 30 about a central axis, centered on the test channels 110 and to begin the clotting test. This action causes the spherical members 114 within the cartridge 30 to roll from one end of the test channel to the other end in a uniform manner. With each agitation cycle, the spherical members 114 in each test channel pass over the sensors 54 associated with each channel 110 to generate a signal that is proportional to the viscosity of the blood sample within each test channel 110. The sensors 54 transmit the generated signals to the controller 20.

As noted above, the device 10 utilizes a non-contact method of detecting the motion and travel time of the spherical members 114 within the cartridge channels. The current method utilizes the magnetic properties of the 400 series stainless steel ball; however, other non-contact detection methods may be used, such as ultrasonic, electromagnetic, optical, etc.

Each sensor 54 includes a pair of neodymium-iron-boron rare earth magnets 118 and two Hall-Effect sensors 122 for each channel 110. Each magnet 118, separated by approximately 9.5 mm along the linear path of each test channel creates a localized magnetic field through the Hall-Effect sensor 122 and into the specific region of the cartridge 30. When the magnetic stainless steel ball passes through the magnetic field, the Hall-Effect sensor 122 detects the change in flux above a quiescent baseline signal caused by the presence of magnetic ball and generates a voltage. The device measures the baseline (quiescent) magnetic signal at the beginning of each cycle. The voltage from each sensor 54 (if there is a voltage detected) is transmitted to the controller 20 for further processing.

Other excitation sources and sensor technologies could be employed to measure the coagulation effect in each channel; however, they may be subject to channel-to-channel crosstalk. Ultrasonic sensors for each channel could also be used. In this case, the spherical members 114 in each channel would not be required to be magnetic, but of a density much greater than whole blood, so that the ultrasonic reflection would be large enough to receive a signal. Electromagnetic sensors, similar to miniature metal detectors, could also be used. In this case, the spherical members would need to be electrically conductive, but not magnetic. Optical detection of the spherical members could be used. In this case, reflective sensor elements that provide an excitation light source and an adjacent light detector would detect the reflection of the spherical members as they pass over the optical sensor. The advantage of the use of magnetic sensing is that the magnetic fields between channels are self-isolating, due to the fact that they are all of the same polarity and do not interfere with adjacent channels as close at 4 mm apart.

During the first minutes of the testing, the baseline or normal viscosity of the sample aliquots is established. As fibrin begins to form in each of the test channels, an increase in viscosity of between 10% and 20% is observed and recorded by the controller 20. Shortly after this increase, the coagulation cascade progresses rapidly to the point where the viscosity of the sample in a given channel is greater than the spherical member's ability to travel through the sample. The sensors 54 in line with the specific channel 110 sense that there is no longer a voltage being generated. The controller 20 interprets this as clot formation and records the time of the clot. The test proceeds until all channels have clotted or the pre-programmed maximum test time has been achieved (e.g., the test is complete at 236).

As described earlier, clot integrity or strength is also considered when considering clotting time and the determination of a complete clot. Only those clotting times that are associated with a firm clot are considered in determining the source of coagulopathy. Physical observation of weak clots show small fibers formed around the spherical member that inhibit the sphere from traversing the entire length of the test channel; however, the spherical member is able to move a short distance and across one of the two sensors in the test channel. By contrast, a high integrity clot captures the spherical member completely and allows for little or no travel after clot formation.

After clot formation, the sensor signals can assess clot integrity. Clot formation is determined when the sensors 54 no longer see the two sensor peaks in each device agitation cycle. In a clot of high integrity/strength, neither sensor 54 produces a signal after clot formation. In a weak clot of low integrity, one of the sensors 54 continues to produce a signal, indicating that the clot is allowing the spherical member 114 to travel over a limited distance. Clot integrity is quantified by looking at the average signal in the channel from the time the clot is initially formed, when at least one sensor reports no signal, until the end of the programmable testing period of between 300 and 1,800 seconds. The lower the number, the higher the clot integrity. A high integrity clot gives a value of between zero and 100. A moderate integrity clot gives a value between 101 and 400. Low integrity clots yield clot strength values greater than 401 and as high as 2,000.

The device 10 compares the clotting times and clot integrity to two (2) untreated or reference channels within the cartridge 30 to the therapy containing channels. Other clotting tests determine clotting times in seconds and compare to an established range of clotting times. The device 10 looks at clotting times relative to the reference sample channels, in the form of a clotting time ratio, as a way of determining the response to the various hemostatic agents. A value of 1.0 indicates no difference between the hemostatic agent and reference sample channels. A value below 1.0 indicates a reduction in clotting time as compared to the reference channels and a value greater than 1.0 indicates a prolongation of clotting time. The coefficient of variation (CV) in clotting times may be as high as 12%, so the threshold for a 'response' to a reagent is based on a reduction greater than the CV. A reduction in clotting time, normalized to the reference channels, of greater than 20% with a clot of high integrity (equal to or less than 100), is considered a valid response to the reagents within a specific channel. If the clotting time for a test chamber is below the lower limit of an established normal range (typically between 120 and 270 seconds), the chamber results are flagged as potentially hypercoagulable. If the clotting time is above the upper limit of the established normal range, the test chamber is flagged as hypocoagulable.

Figure 12:
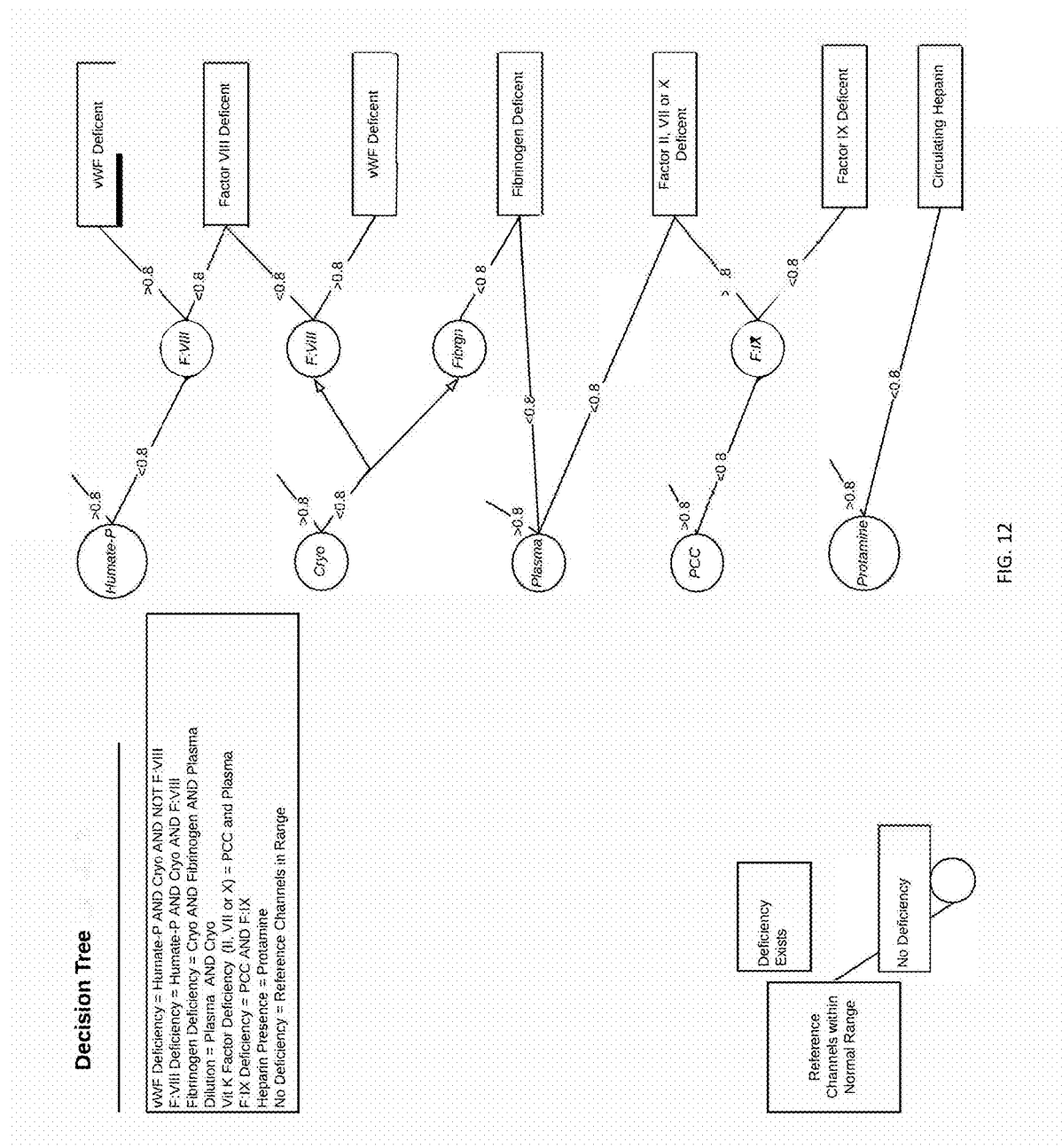
FIG. 12 is a decision tree for determining cause of coagulopathy based on response to hemostatic reagents.

The etiology of coagulopathy is determined by the clotting time ratios described and clot strength of each test chamber 110 as compared to reference sample aliquots included within the cartridge 30. Information for hemostatic agents that reduce clotting time as well as hemostatic agents that do not reduce clotting time are combined to isolate either a specific etiology or a probable group of factors that are deficient and thereby causing the coagulopathy. For example, with reference to the decision tree in FIG. 12, if a cartridge 30 and sample responds with reduced clotting time (indicated by the <0.8 ratio) in the cryoprecipitate channels, but does not respond in the Factor VIII channels (indicated by the >0.8 ratio), then the deficiency is likely to be von Willebrand Factor or fibrinogen, since cryoprecipitate contains all three coagulation factors. Likewise, if the sample responds to the fibrinogen channels and the cryoprecipitate channels but does not respond to the Factor VIII or Factor VIII/vWF complex channels, then the determination is likely to be a fibrinogen deficiency.

These responses to the various hemostatic agents create patterns or signatures that are indicative of specific conditions that are reported at the end of the testing sequence. The display 26 can provide a visual indication of each channel's clotting time and the ratio to the untreated reference channels. The display 26 also can provide the resulting deficiencies or diagnosis, subject to interpretation by a physician, regarding the possible cause of the coagulopathy, based upon clotting times, clotting ratios and clot strength across all test channels. The analysis performed by the controller is multi-variate in nature, looking at all channel data in determining the etiology of coagulopathy. The device 10 may also include a printer to print the information and data provided on the display 26. Response to therapy is established by a threshold of the ratios to the reference channels. Since there is inherent variation across channels of up to 12%, the thresholds are established to take this into account. Response to a hemostatic reagent is defined as a ratio greater than a predetermined threshold (e.g., a change of 20% or more as compared to a reference channel).

The device 10 may also be used in testing how a clot breaks up after clot formation has been established. Normally, there is a process called fibrinolysis where a blood clot dissolves naturally. In device 10 described herein, the cartridge 30 could continue to agitate for about 30-60 minutes while monitoring for the spherical members 114 to resume movement. While this should not occur in a normal sample, some patients, for example trauma patients may experience hyperfibrinolysis, where the clots dissolve too quickly and bleeding starts up again.

Initial agitation cycles of between 1 and 2 seconds allow sufficient time for the spherical members 114 to traverse from one end of the cartridge 30 to the other. As clot formation begins, the viscosity of the sample aliquot increases, causing the travel time to increase. The device has the ability to apply an adaptive approach to the agitation cycle parameters.

For reasons of completeness, various aspects of the invention are set out in the following numbered clauses:

Clause 1. A system comprising:
a cartridge comprising a whole blood sample, the cartridge including a plurality of test chambers and a metal sphere in each test chamber;
a device configured to receive the cartridge, the device including
a plurality of sensors, each sensor positioned adjacent to one of the test chambers, and
a controller configured to
activate a vacuum source to move a portion of the whole blood sample into each of the test chambers,
move the cartridge,
receive signals from each of the sensors while the cartridge is moving,
determine whether the metal sphere is moving in the test chamber, and determine whether the whole blood sample in each test chamber exhibits coagulopathy, and output an indicator whether coagulopathy is present in the whole blood for each test chamber on a display.

Clause 2. The system of clause 1, wherein each sensor includes a magnet and a Hall-effect sensor.

Clause 3. The system of clause 2, wherein the magnet generates a magnetic field near its associated test chamber, and wherein the metal sphere in the test chamber generates a disturbance in the magnetic field, and wherein the sensor detects the disturbance and transmits a signal to the controller to determine whether the sphere is moving in the test chamber.

Clause 4. The system of clause 1, further comprising a plurality of vacuum ports in the cartridge selectively coupled to the vacuum source, and further comprising a plurality of hydrophobic filters in line with each of the vacuum ports.

Clause 5. The system of clause 4, wherein the cartridge includes a plurality of reagent chambers, one reagent chambers associated with one of the test chambers, and wherein the hydrophobic filters are configured to stop the flow of blood when each of the reagent chambers is filled.

Clause 6. The system of clause 5, wherein the device further comprises a heating element configured to apply thermal energy to the cartridge and to the whole blood sample.

Clause 7. The system of clause 6, wherein the heating element heats the whole blood sample to a temperature between 34 degrees Celsius and 37 degrees Celsius Clause 8. The system of clause 6, wherein the heating element heats the whole blood sample to a temperature between 30 degrees Celsius and 33 degrees Celsius.

Clause 9. The system of clause 7, wherein the whole blood sample is mixed with a reagent in each of the reagent chambers and incubated between 1 minute and 10 minutes.

Clause 10. The system of clause 9, wherein the reagents in each of the reagent chambers is isolated from its adjacent reagent chambers.

Clause 11. The system of clause 1, wherein the controller is further configured to determine a length of time to clot formation in each of the test chambers.

Clause 12. The system of clause 11, wherein the length of time is based on how long the sensor associated with one of the test chambers detects movement of the metal sphere.

Clause 13. The system of clause 1, wherein each test chamber includes two of the sensors.

Clause 14. The system of clause 13, wherein the controller is further configured to determine clot formation.

Clause 15. The system of clause 14, wherein clot formation is determined when the controller detects the absence of two peaks in each agitation cycle and is indicative that the metal sphere has stopped moving within the test chamber.

Clause 16. The system of clause 14, wherein the controller is further configured to determine clot integrity.

Clause 17. The system of clause 16, wherein a clot of high integrity is determined where neither one of the two sensors generates a signal after the clot formation.

Clause 18. The system of clause 16, wherein a clot of low integrity is determined where one of the two sensors continues to generate a signal indicating that the clot is allowing the metal sphere to move over a limited distance.

Clause 19. The system of clause 16, wherein clot integrity is based on an average signal in the test chamber generated by the two sensors from the time the clot formed to the end of the test.

Clause 20. The system of clause 5, wherein the cartridge includes 18 test chambers.

Clause 21. The system of clause 20, wherein each of the 18 test chambers is associated with one of the reagent chambers, and wherein each of the 18 test chambers receives a whole blood-reagent complex from the associated reagent chamber.

Clause 22. The system of clause 1, wherein the metal sphere in each test chamber passes over the sensor associated with each test chamber to generate a signal that is proportional to the viscosity of the whole blood sample within each test chamber.

Clause 23. The system of clause 1, wherein the controller is further configured to determine a diagnosis based on results of the coagulopathy.

Clause 24. The system of clause 23, wherein the controller is further configured to output the diagnosis on the display.

Clause 25. A device for processing a cartridge containing a whole blood sample, the device comprising:

a recess for receiving the cartridge, a vacuum source coupled to the cartridge, an actuator linked to the cartridge to agitate the cartridge; and a controller configured to activate the vacuum source to move the whole blood sample from a container into a plurality of channels in the cartridge and subsequently into a plurality of reagent chambers where the blood mixes with a reagent, and then through a plurality of serpentine-shaped channels to a plurality of test chambers, activate the actuator to agitate the cartridge, receive signals from a plurality of sensors, each sensor associated with one of the test chambers, where the signals are based on the presence of a spherical member within a magnetic field generated by a magnet positioned adjacent to each of the test chambers, determine whether coagulopathy is present in the whole blood for each test chamber, and output an indicator whether coagulopathy is present in the whole blood for each test chamber on a display.

Clause 26. The device of clause 25, further comprising a plurality of vacuum ports in the cartridge selectively coupled to the vacuum source, and further comprising a plurality of hydrophobic filters in line with each of the vacuum ports, the hydrophobic filters configured to stop the flow of blood when each of the reagent chambers is filled.

Clause 27. The device of clause 25, further comprising a heating element configured to apply thermal energy to the cartridge and to the whole blood sample.

Clause 28. The device of clause 27, wherein the heating element heats the whole blood sample to a temperature between 34 degrees Celsius and 37 degrees Celsius Clause 29. The device of clause 27, wherein the heating element heats the whole blood sample to a temperature between 30 degrees Celsius and 33 degrees Celsius.

Clause 30. The device of clause 28, wherein the whole blood sample is mixed with a reagent in each of the reagent chambers and incubated between 1 minute and 10 minutes.

Clause 31. The device of clause 30, wherein the reagents in each of the reagent chambers is isolated from its adjacent reagent chambers.

Clause 32. The device of clause 25, wherein the controller is further configured to determine a length of time to clot formation in each of the test chambers.

Clause 33. The device of clause 32, wherein the length of time is based on how long the sensor associated with one of the test chambers detects movement of the spherical member.

Clause 34. The device of clause 25, wherein each test channel includes two of the sensors.

Clause 35. The device of clause 34, wherein the controller is further configured to determine clot formation.

Clause 36. The device of clause 35, wherein clot formation is determined when the controller detects the absence of two peaks in each agitation cycle and is indicative that the spherical member has stopped moving within the test chamber.

Clause 37. The device of clause 35, wherein the controller is further configured to determine clot integrity.

Clause 38. The device of clause 37, wherein a clot of high integrity is determined where neither one of the two sensors generates a signal after the clot formation.

Clause 39. The device of clause 37, wherein a clot of low integrity is determined where one of the two sensors continues to generate a signal indicating that the clot is allowing the spherical member to move over a limited distance.

Clause 40. The device of clause 37, wherein clot integrity is based on an average signal in the test chamber generated by the two sensors from the time the clot formed to the end of the test.

Clause 41. The device of clause 25, wherein the cartridge includes 18 test chambers.

Clause 42. The device of clause 41, wherein each of the 18 test chambers is associated with one of the reagent chambers, and wherein each of the 18 test chambers receives a whole blood-reagent complex from the associated reagent chamber.

Clause 43. The device of clause 25, wherein the spherical member in each test chamber passes over the sensors associated with each test chamber to generate a signal that is proportional to the viscosity of the whole blood sample within each test chamber.

Clause 44. The device of clause 25, wherein the controller is further configured to determine a diagnosis based on results of the coagulopathy.

Clause 45. The device of clause 25, wherein the controller is further configured to output the diagnosis on the display.

Clause 46. A method of determining clotting characteristics of a whole blood sample, the method comprising:
introducing the whole blood sample into a cartridge having a plurality of test channels, wherein each test channel includes a reagent chamber, a test chamber, and a metal sphere in each test chamber;
mixing the whole blood sample with a reagent in each of the reagent chambers;
agitating the cartridge;
detecting movement of the metal sphere in each of the test chambers with two sensors positioned adjacent to each of the test chambers;
determining, with a controller, one or more clot characteristics of the whole blood sample based on detection of movement of the metal sphere; and
generating an indicator of the clot characteristic for display to a user.

Clause 47. The method of claim 46, further comprising reversing an anti-coagulant in the whole blood sample prior to the whole blood sample entering the test chambers;

Clause 48. The method of claim 47, wherein the cartridge includes calcium, and further wherein the whole blood sample contacts the calcium between an outlet of the reagent chamber and an inlet of the test chamber.

Clause 49. The method of claim 46, wherein determining the one or more clot characteristics includes determining clot formation of the whole blood sample.

Clause 50. The method of claim 49, wherein determining clot formation includes the controller detecting an absence of two peaks in each agitation cycle which is indicative that the metal sphere has stopped moving within the test chamber.

Clause 51. The method of claim 50, wherein one of the clot characteristics is clot integrity.

Clause 52. The method of claim 51, wherein a clot of high integrity is determined where neither one of the two sensors generates a signal after the clot formation.

Clause 53. The method of claim 51, wherein a clot of low integrity is determined where one of the two sensors continues to generate a signal indicating that the clot is allowing the metal sphere to move over a limited distance.

Clause 54. The method of claim 51, wherein clot integrity is based on an average signal in the test chamber generated by the two sensors from the time the clot formed to the end of the test.

Clause 55. The method of claim 51, wherein agitating the cartridge includes rocking the cartridge at a predetermined duty cycle, and wherein a duty cycle of the metal sphere is based on detection of movement of the metal sphere Clause 56. The method of claim 55, wherein the duty cycle of the metal sphere is proportional to the clot integrity.

Clause 57. The method of claim 56, where the clot integrity is low when the duty cycle of the metal sphere is greater than 40%.

Clause 58. The method of claim 56, wherein the clot integrity is medium when the duty cycle of the metal sphere is between 25% and 40%.

Clause 59. The method of claim 56, wherein the clot integrity is high when the duty cycle of the metal sphere is between 10% and 25%.

Clause 60. The method of claim 56, wherein the clot integrity is very high when the duty cycle of the metal sphere is between 0% and 10%.

Clause 61. The method of claim 46, wherein determining the one or more clot characteristics includes determining viscosity of the whole blood sample.

Clause 62. The method of claim 61, wherein the viscosity is based on travel time of the metal sphere between the two sensors.

Clause 63. The method of claim 62, wherein the viscosity increases as a clot forms in the whole blood sample.

Clause 64. The method of claim 63, wherein clot formation begins when viscosity is between 10% and 20% of a predetermined baseline.

It is understood that the foregoing detailed description is merely illustrative and is not to be taken as limitations upon the scope of the invention, which is defined solely by the appended claims and their equivalents.

Various changes and modifications to the disclosed embodiments will be apparent to those skilled in the art. Various features and advantages of the invention are set forth in the following claims.

What is claimed is:

1. A system comprising:
a cartridge comprising a whole blood sample, the cartridge including a plurality of test chambers and a metal sphere in each test chamber;
a device configured to receive the cartridge, the device including
a plurality of sensors, each sensor positioned adjacent to one of the test chambers, and a controller configured to
activate a vacuum source to move a portion of the whole blood sample into each of the test chambers,
move the cartridge,
receive signals from each of the sensors while the cartridge is moving,
determine whether the metal sphere is moving in the test chamber, and
determine whether the whole blood sample in each test chamber exhibits coagulopathy, and
output an indicator whether coagulopathy is present in the whole blood for each test chamber on a display.

2. The system of claim 1, wherein each sensor includes a magnet and a Hall-effect sensor.

3. The system of claim 2, wherein the magnet generates a magnetic field near its associated test chamber, and wherein the metal sphere in the test chamber generates a disturbance in the magnetic field, and wherein the sensor detects the disturbance and transmits a signal to the controller to determine whether the sphere is moving in the test chamber.

4. The system of claim 1, further comprising a plurality of vacuum ports in the cartridge selectively coupled to the vacuum source, and further comprising a plurality of hydrophobic filters in line with each of the vacuum ports.

5. The system of claim 4, wherein the cartridge includes a plurality of reagent chambers, one reagent chambers associated with one of the test chambers, and wherein the hydrophobic filters are configured to stop the flow of blood when each of the reagent chambers is filled.

6. The system of claim 5, wherein the device further comprises a heating element configured to apply thermal energy to the cartridge and to the whole blood sample.

7. The system of claim 6, wherein the heating element heats the whole blood sample to a temperature between 34 degrees Celsius and 37 degrees Celsius.

8. The system of claim 6, wherein the heating element heats the whole blood sample to a temperature between 30 degrees Celsius and 33 degrees Celsius.

9. The system of claim 7, wherein the whole blood sample is mixed with a reagent in each of the reagent chambers and incubated between 1 minute and 10 minutes.

10. The system of claim 9, wherein the reagents in each of the reagent chambers is isolated from its adjacent reagent chambers.

11. The system of claim 1, wherein the controller is further configured to determine a length of time to clot formation in each of the test chambers.

12. The system of claim 11, wherein the length of time is based on how long the sensor associated with one of the test chambers detects movement of the metal sphere.

13. The system of claim 1, wherein each test chamber includes two of the sensors.

14. The system of claim 13, wherein the controller is further configured to determine clot formation.

15. The system of claim 14, wherein clot formation is determined when the controller detects the absence of two peaks in each agitation cycle and is indicative that the metal sphere has stopped moving within the test chamber.

16. The system of claim 14, wherein the controller is further configured to determine clot integrity.

17. The system of claim 16, wherein a clot of high integrity is determined where neither one of the two sensors generates a signal after the clot formation.

18. The system of claim 16, wherein a clot of low integrity is determined where one of the two sensors continues to generate a signal indicating that the clot is allowing the metal sphere to move over a limited distance.

19. The system of claim 16, wherein clot integrity is based on an average signal in the test chamber generated by the two sensors from the time the clot formed to the end of the test.

20. The system of claim 5, wherein the cartridge includes 18 test chambers.

21. The system of claim 20, wherein each of the 18 test chambers is associated with one of the reagent chambers, and wherein each of the 18 test chambers receives a whole blood-reagent complex from the associated reagent chamber.

22. The system of claim 1, wherein the metal sphere in each test chamber passes over the sensor associated with each test chamber to generate a signal that is proportional to the viscosity of the whole blood sample within each test chamber.

23. The system of claim 1, wherein the controller is further configured to determine a diagnosis based on results of the coagulopathy.

24. The system of claim 23, wherein the controller is further configured to output the diagnosis on the display.

* * * * *